(12) United States Patent
Thomas et al.

(10) Patent No.: US 8,262,730 B2
(45) Date of Patent: Sep. 11, 2012

(54) METHODS OF BONDING OR MODIFYING HYDROGELS USING IRRADIATION

(75) Inventors: Brian Thomas, Columbia City, IN (US); Kai Zhang, Warsaw, IN (US); Garryl Hudgins, Burnsville, MN (US); Robert Hodorek, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1669 days.

(21) Appl. No.: 11/608,128

(22) Filed: Dec. 7, 2006

(65) Prior Publication Data

US 2007/0134333 A1 Jun. 14, 2007

Related U.S. Application Data

(60) Provisional application No. 60/748,293, filed on Dec. 7, 2005.

(51) Int. Cl.
*A61F 2/02* (2006.01)
*A61F 2/28* (2006.01)
*A61F 2/30* (2006.01)

(52) U.S. Cl. ............... 623/11.11; 623/13.11; 623/16.11; 623/18.11; 523/113

(58) Field of Classification Search ............. 424/78.3, 424/486; 156/272.2; 523/113; 528/354; 623/13.11
See application file for complete search history.

(56) References Cited

U.S. PATENT DOCUMENTS

| | | |
|---|---|---|
| 3,200,178 A | 8/1965 | Kanji |
| 3,862,265 A | 1/1975 | Steinkamp |
| 3,875,302 A | 4/1975 | Inoue |
| 4,036,788 A | 7/1977 | Steckler |
| 4,058,491 A | 11/1977 | Steckler |
| 4,060,678 A | 11/1977 | Steckler |
| 4,071,508 A | 1/1978 | Steckler |
| 4,279,795 A | 7/1981 | Yamashita |
| 4,300,820 A | 11/1981 | Shah |
| 4,379,874 A | 4/1983 | Stoy |
| 4,451,599 A | 5/1984 | Odorzynski |
| 4,451,630 A | 5/1984 | Atkinson |
| 4,464,438 A | 8/1984 | Lu |
| 4,472,542 A | 9/1984 | Nambu |
| 4,640,941 A | 2/1987 | Park |
| 4,656,216 A | 4/1987 | Muller |
| 4,663,358 A | 5/1987 | Hyon |

(Continued)

FOREIGN PATENT DOCUMENTS

EP 0256293 2/1988

(Continued)

OTHER PUBLICATIONS

Chow et al., Ocacalcium Phosphate Monograph in Oral Science, vol. 18, pp. 94-111 and 130-147.

(Continued)

*Primary Examiner* — Melanie Hand
(74) *Attorney, Agent, or Firm* — Schwegman Lundberg & Woessner, P.A.

(57) ABSTRACT

This invention provides methods and processes to attach or bond hydrogels to suitable surfaces using irradiation techniques and also provides methods and processes to create crosslinked regions in hydrogel articles using these irradiation techniques. Specifically, lasers at wavelengths tuned to the irradiation absorption bands of hydroxyl groups, carboxylic acid groups or water may be used to attach or bond hydrogels to surfaces such as soft tissue and hydrogel surfaces or to crosslink regions in hydrogel articles.

20 Claims, 2 Drawing Sheets

U.S. PATENT DOCUMENTS

| | | |
|---|---|---|
| 4,664,857 A | 5/1987 | Nambu |
| 4,699,146 A | 10/1987 | Sieverding |
| 4,734,097 A | 3/1988 | Tanabe |
| 4,771,089 A | 9/1988 | Ofstead |
| 4,772,287 A | 9/1988 | Ray |
| 4,808,353 A | 2/1989 | Nambu |
| 4,842,597 A | 6/1989 | Brook |
| 4,851,168 A | 7/1989 | Graiver |
| 4,859,719 A | 8/1989 | Ofstead |
| 4,871,490 A | 10/1989 | Rosiak |
| 4,874,562 A | 10/1989 | Hyon et al. |
| 4,915,974 A | 4/1990 | D'Amelia |
| 4,956,122 A | 9/1990 | Watts et al. |
| 4,966,924 A | 10/1990 | Hyon |
| 4,988,761 A | 1/1991 | Ikada |
| 5,028,648 A | 7/1991 | Famili |
| 5,047,055 A | 9/1991 | Bao |
| 5,053,455 A | 10/1991 | Kroggel |
| 5,106,876 A | 4/1992 | Kawamura |
| 5,118,779 A | 6/1992 | Szycher |
| 5,122,565 A | 6/1992 | George |
| 5,157,093 A | 10/1992 | Harisiades |
| 5,189,097 A | 2/1993 | LaFleur |
| 5,192,326 A | 3/1993 | Bao |
| 5,244,799 A | 9/1993 | Anderson |
| 5,276,079 A | 1/1994 | Duan et al. |
| 5,288,503 A | 2/1994 | Wood |
| 5,306,311 A | 4/1994 | Stone |
| 5,311,223 A | 5/1994 | Vanderlaan |
| 5,315,478 A | 5/1994 | Cadwell |
| 5,334,634 A | 8/1994 | Bastiolo |
| 5,336,551 A | 8/1994 | Graiver |
| 5,358,525 A | 10/1994 | Fox |
| 5,360,830 A | 11/1994 | Bastiolo |
| 5,362,803 A | 11/1994 | LaFleur |
| 5,364,547 A | 11/1994 | Babb et al. |
| 5,407,055 A | 4/1995 | Tanaka |
| 5,409,966 A | 4/1995 | Duan et al. |
| 5,410,016 A * | 4/1995 | Hubbell et al. ............... 528/354 |
| 5,458,643 A | 10/1995 | Oka |
| 5,527,271 A | 6/1996 | Shah |
| 5,540,033 A | 7/1996 | Fox |
| 5,552,096 A | 9/1996 | Auda |
| 5,576,072 A | 11/1996 | Hostettler |
| 5,580,938 A | 12/1996 | Gutweiller |
| 5,624,463 A | 4/1997 | Stone |
| 5,632,774 A | 5/1997 | Babian |
| 5,674,295 A | 10/1997 | Ray |
| 5,681,300 A | 10/1997 | Ahr |
| 5,705,296 A | 1/1998 | Kamauchi |
| 5,709,854 A | 1/1998 | Griffith-Cima |
| 5,711,960 A | 1/1998 | Shikinami |
| 5,716,404 A | 2/1998 | Vacanti |
| 5,723,331 A | 3/1998 | Tubo |
| 5,834,029 A | 11/1998 | Bellamkonda |
| 5,846,214 A | 12/1998 | Makuuchi et al. |
| 5,879,713 A | 3/1999 | Roth et al. |
| 5,891,826 A | 4/1999 | Tsaur et al. |
| 5,941,909 A | 8/1999 | Purkait |
| 5,976,186 A | 11/1999 | Bao |
| 5,981,826 A | 11/1999 | Ku |
| 6,015,576 A | 1/2000 | See |
| 6,017,577 A | 1/2000 | Hostettler |
| 6,040,493 A | 3/2000 | Cooke |
| 6,080,488 A | 6/2000 | Hostettler |
| 6,117,449 A | 9/2000 | See |
| 6,120,904 A | 9/2000 | Hostettler |
| 6,121,341 A | 9/2000 | Sawhney |
| 6,129,761 A | 10/2000 | Hubbell |
| 6,132,468 A | 10/2000 | Mansmann |
| 6,139,963 A | 10/2000 | Fujii |
| 6,146,686 A | 11/2000 | Leitao |
| 6,156,345 A | 12/2000 | Chudzik |
| 6,156,572 A | 12/2000 | Bettamkonda |
| 6,162,456 A | 12/2000 | Dunbar |
| 6,180,132 B1 | 1/2001 | Huang |
| 6,180,606 B1 | 1/2001 | Chen |
| 6,184,197 B1 | 2/2001 | Heinzman |
| 6,187,048 B1 | 2/2001 | Milner |
| 6,207,185 B1 | 3/2001 | See et al. |
| 6,211,296 B1 | 4/2001 | Frate |
| 6,224,893 B1 | 5/2001 | Langer |
| 6,231,605 B1 | 5/2001 | Ku |
| 6,232,406 B1 | 5/2001 | Stoy et al. |
| 6,238,691 B1 | 5/2001 | Huang |
| 6,268,405 B1 | 7/2001 | Yao |
| 6,271,278 B1 | 8/2001 | Park et al. |
| 6,280,475 B1 | 8/2001 | Bao |
| 6,306,424 B1 | 10/2001 | Vyakamam |
| 6,365,149 B2 | 4/2002 | Vyakamam |
| 6,371,984 B1 | 4/2002 | Van Dyke |
| 6,372,283 B1 | 4/2002 | Shim |
| 6,375,634 B1 | 4/2002 | Carroll |
| 6,387,325 B1 | 5/2002 | Keusch |
| 6,402,784 B1 | 6/2002 | Wardlaw |
| 6,443,988 B2 | 9/2002 | Felt |
| 6,509,098 B1 | 1/2003 | Merrill |
| 6,531,147 B2 | 3/2003 | Sawhney |
| 6,533,817 B1 | 3/2003 | Norton |
| 6,583,219 B2 | 6/2003 | Won |
| 6,602,952 B1 | 8/2003 | Bentley |
| 6,608,117 B1 | 8/2003 | Gvozdic |
| 6,620,196 B1 | 9/2003 | Trieu |
| 6,626,945 B2 | 9/2003 | Simon |
| 6,629,997 B2 | 10/2003 | Mansmann |
| 6,630,457 B1 | 10/2003 | Aeschlimann |
| 6,632,246 B1 | 10/2003 | Simon |
| 6,645,517 B2 | 11/2003 | West |
| 6,692,738 B2 | 2/2004 | MacLaughlin |
| 6,706,690 B2 | 3/2004 | Reich |
| 6,709,668 B2 | 3/2004 | Won |
| 6,710,104 B2 | 3/2004 | Haraguchi |
| 6,710,126 B1 | 3/2004 | Hirt |
| 6,723,781 B1 | 4/2004 | Frate |
| 6,730,298 B2 | 5/2004 | Griffith-Cima |
| 6,733,533 B1 | 5/2004 | Lozier |
| 6,780,840 B1 | 8/2004 | DeVore |
| 6,783,546 B2 | 8/2004 | Zucherman |
| 6,783,721 B2 | 8/2004 | Higham |
| 6,803,420 B2 | 10/2004 | Cleary |
| 6,852,772 B2 | 2/2005 | Muratoglu |
| 6,855,743 B1 | 2/2005 | Gvozdic |
| 6,861,067 B2 | 3/2005 | McGhee |
| 7,235,592 B2 | 6/2007 | Muratoglu |
| 7,531,000 B2 | 5/2009 | Hodorek |
| 2001/0026810 A1 | 10/2001 | McGhee |
| 2001/0032019 A1 | 10/2001 | Van Dyke |
| 2001/0049417 A1 | 12/2001 | Frate |
| 2001/0053897 A1 | 12/2001 | Frate et al. |
| 2002/0022884 A1 | 2/2002 | Mansmann |
| 2002/0026244 A1 | 2/2002 | Trieu |
| 2002/0029083 A1 | 3/2002 | Zucherman |
| 2002/0049498 A1 | 4/2002 | Yuksel |
| 2002/0131952 A1 | 9/2002 | Hennink |
| 2002/0151979 A1 | 10/2002 | Lambrecht |
| 2002/0173855 A1 | 11/2002 | Mansmann |
| 2002/0193531 A1 | 12/2002 | Stoy |
| 2003/0008396 A1 | 1/2003 | Ku |
| 2003/0065389 A1 | 4/2003 | Petersen |
| 2003/0080465 A1 | 5/2003 | Higham |
| 2003/0099709 A1 | 5/2003 | Shah |
| 2003/0130427 A1 | 7/2003 | Cleary |
| 2003/0152528 A1 | 8/2003 | Singh et al. |
| 2003/0170308 A1 | 9/2003 | Cleary |
| 2003/0195628 A1 | 10/2003 | Bao |
| 2003/0232895 A1 | 12/2003 | Omidian |
| 2003/0236323 A1 | 12/2003 | Ratner |
| 2004/0002764 A1 | 1/2004 | Gainor |
| 2004/0005423 A1 | 1/2004 | Dalton |
| 2004/0030392 A1 | 2/2004 | Lambrecht |
| 2004/0039447 A1* | 2/2004 | Simon et al. ............... 623/13.11 |
| 2004/0092653 A1 | 5/2004 | Ruberti |
| 2004/0096509 A1 | 5/2004 | Hutchens |
| 2004/0116641 A1 | 6/2004 | Mather |
| 2004/0121951 A1 | 6/2004 | Rhee |
| 2004/0127618 A1 | 7/2004 | Ulmer |
| 2004/0127992 A1 | 7/2004 | Serhan et al. |

| | | | | | | |
|---|---|---|---|---|---|---|
| 2004/0131582 A1* | 7/2004 | Grinstaff et al. ............. 424/78.3 | WO | 03008007 | 1/2003 | |
| 2004/0131852 A1 | 7/2004 | Grinstaff | WO | 03074099 | 9/2003 | |
| 2004/0133280 A1 | 7/2004 | Trieu | WO | 03092359 | 10/2003 | |
| 2004/0143329 A1 | 7/2004 | Ku | WO | WO 03/082359 | 10/2003 | |
| 2004/0147673 A1 | 7/2004 | Calabro | WO | 2004007651 | 1/2004 | |
| 2004/0153163 A1 | 8/2004 | Posner | WO | 2004029174 | 4/2004 | |
| 2004/0161444 A1 | 8/2004 | Song | WO | 2004031253 | 4/2004 | |
| 2004/0171740 A1 | 9/2004 | Ruberti | WO | 2004047690 | 6/2004 | |
| 2004/0199250 A1 | 10/2004 | Fell | WO | 2004055057 | 7/2004 | |
| 2004/0220296 A1* | 11/2004 | Lowman et al. ............. 523/113 | WO | 2004060427 | 7/2004 | |
| 2004/0242770 A1 | 12/2004 | Feldstein | WO | 2004063388 | 7/2004 | |
| 2004/0244978 A1 | 12/2004 | Shaarpour | WO | 2004064693 | 8/2004 | |
| 2005/0004560 A1 | 1/2005 | Cox | WO | 2004066704 | 8/2004 | |
| 2005/0008828 A1 | 1/2005 | Libera et al. | WO | 2004069296 | 8/2004 | |
| 2005/0027069 A1 | 2/2005 | Rhee et al. | WO | 2004072138 | 8/2004 | |
| 2005/0048103 A1 | 3/2005 | Cleary | WO | 2004093786 | 11/2004 | |
| 2005/0049365 A1 | 3/2005 | Cleary | WO | 2005004943 | 1/2005 | |
| 2005/0075454 A1 | 4/2005 | Plochocka et al. | WO | WO2005004943 | 1/2005 | |
| 2005/0095296 A1 | 5/2005 | Lowman | WO | 2005035726 A2 | 4/2005 | |
| 2005/0107561 A1 | 5/2005 | Lee et al. | WO | WO 2005/030832 | 4/2005 | |
| 2005/0197441 A1 | 9/2005 | Shibutani | WO | WO2005030382 | 4/2005 | |
| 2006/0078587 A1 | 4/2006 | Leong | WO | WO 2005035726 A2 * | 4/2005 | |
| 2006/0141002 A1 | 6/2006 | Liu | WO | 2006021054 A1 | 3/2006 | |
| 2006/0188487 A1 | 8/2006 | Thomas | WO | 2006091706 | 8/2006 | |
| 2007/0004861 A1 | 1/2007 | Cai | WO | 2007067697 | 6/2007 | |
| 2007/0202323 A1 | 8/2007 | Kleiner | WO | 2007015208 | 8/2007 | |
| 2007/0293651 A1 | 12/2007 | Tada | WO | WO 2008/144514 | 11/2008 | |
| 2008/0090145 A1 | 4/2008 | Hiwara | WO | 2009020793 | 2/2009 | |
| 2009/0053318 A1 | 2/2009 | Tan | WO | WO 2009/032430 | 3/2009 | |
| | | | WO | WO 2009/088654 | 7/2009 | |

FOREIGN PATENT DOCUMENTS

| | | |
|---|---|---|
| EP | 0290616 | 11/1988 |
| EP | 0365108 | 4/1990 |
| EP | 0505634 | 9/1992 |
| EP | 0696210 | 2/1996 |
| EP | 0738762 | 4/1996 |
| EP | 0784987 | 7/1997 |
| EP | 0835143 | 4/1998 |
| EP | 0845480 | 6/1998 |
| EP | 0927053 | 7/1999 |
| EP | 1079224 | 2/2001 |
| EP | 1174463 | 1/2002 |
| EP | 1209492 | 5/2002 |
| EP | 1593400 | 11/2005 |
| EP | 1595899 | 11/2005 |
| FR | 2786400 | 6/2000 |
| FR | 2865939 | 8/2005 |
| FR | 2866571 | 8/2005 |
| GB | 2338958 | 10/2000 |
| JP | 01178545 | 7/1989 |
| JP | 01305959 | 12/1989 |
| JP | 03141957 | 6/1991 |
| JP | 04303444 | 10/1992 |
| JP | 09124730 | 5/1997 |
| JP | 09124731 | 5/1997 |
| JP | 10036524 | 2/1998 |
| JP | 10036534 | 2/1998 |
| JP | 10043286 | 2/1998 |
| JP | 10306534 | 2/1998 |
| WO | 9015082 | 12/1990 |
| WO | WO/94/13235 | 6/1994 |
| WO | 9417851 A1 | 8/1994 |
| WO | WO9502616 | 1/1995 |
| WO | 9526699 | 10/1995 |
| WO | 9640304 | 4/1998 |
| WO | 9817215 | 4/1998 |
| WO | 9853768 | 12/1998 |
| WO | 9903454 | 1/1999 |
| WO | 9913923 | 3/1999 |
| WO | 9967320 | 12/1999 |
| WO | 0117574 | 3/2001 |
| WO | WO 01/19283 | 3/2001 |
| WO | 0177197 | 10/2001 |
| WO | WO01/77197 | 10/2001 |
| WO | WO 02/04570 | 1/2002 |
| WO | 0213871 A2 | 2/2002 |
| WO | 02060501 | 8/2002 |
| WO | 02087642 | 11/2002 |
| WO | 02087645 | 11/2002 |

OTHER PUBLICATIONS

Carey et al., Adv. Org. Chem., Part B., p. 829, 2001.
Hickey et al., "Mesh Size and Diffusive Characteristics of Semicrystalline . . . ", Journal of Membrane Science, 107 (1995), pp. 229-237.
LeGeros R.Z., "Calcium Phosphates in Oral Biology and Medicine," Monograph in Oral Science, vol. 15, pp. 1-201.
EP Search Report for EP Application No. 0500100009.9-2115 dated Mar. 1, 2005.
International Search Report for PCT/US2006/006356 dated Jun. 22, 2006.
International Search Report and Written Opinion for PCT/US2008/071435 dated Feb. 5, 2009.
Preliminary Report on Patentability and Written Opinion for PCT/US2008/086817 dated Jul. 6, 2010.
International Search Report and Written Opinion for PCT/US2008/083213 dated May 8, 2009.
Preliminary Report on Patentability and Written Opinion for PCT/US2006/006356 dated Aug. 28, 2007.
Preliminary Report on Patentability for PCT/US2008/071539 dated Mar. 2, 2010.
Noguchi, et al., Poly(vinyl Alcohol) Hydrogel As an Artificial Articular Cartilage: Evaluation of Biocompatibility, Journal of Applied Biomaterials, vol. 2 101-107 (1991), John Wiley & Sons, Inc.
Hassan, et al., Structure and Applications of Poly(vinyl alcohol) Hydrogels Produced by Conventional Crosslinking or by Freezing/Thawing Methods, Advances in Polymer Science, vol. 153, Springer-Verlag Berlin Heidelberg 2000.
Peppas, et al., Physicochemical Foundations and Structural Design of Hydrogels in Medicine and Biology, Annu. Rev. Biomed. Eng. 2000, 02:9-29.
Taguchi. Chemistry Letters, 711-712 (1998).
Lu et al. Journal of Controlled Release, 57, 291-300 (1999).
West et al. Reactive Polymers, 139-147 (1995).
Green et al. Organic Chemistry Principles and Industrial Practice. Wiley VCH, 2003.
Mondino et al. Rad. Chem. and Phys. 55, 723-726 (1999).
Jagur-Grodzinski in Reactive and Functional Polymers, 39, 99-139 (1999).
Tripathy et al. "Novel Flocculating Agent Based on Sodium Alginate and Acrylamide." European Polymer Journal. 35, 2057-2072 (1999).
Haralabakopoulus et al. J. Appl. Poly. Sci., 69, 1885-1890 (1998).
IPRP From PCT/US2008/071539.
IPRP From PCT/US2008/071435.

Bryant, S.J. et al. "Crosslinking Density Influences Chrondrocyte Metabolism in Dynamically Leaded Photocrosslinked Poly(ethylene glycol) Hydrogels." Ann. Biomed. Eng., Mar. 2004, pp. 407-417, vol. 3, No. 3.

Bryant, S.J. et al. "The Effects if Scaffold thickness on Tissue Engineered Cartilage in Photocrosslinked Poly (ethylene oxide) hydrogels." Biomaterials 22, 2001, pp. 619-628.

Bryant, S.J. et al. "Photocrosslinkable Poly(ethylene oxide) and Poly (vinyl alcohol) Hydrogels for Tissue Engineering Cartilage." 21st Annual Conference and the 1999 Annual Fall Meeting of the Biomedical Engineering Society, Oct. 13-15, 1999, Atlanta, GA; Engineering in Medicine and Biology 1999, p. 751, vol. 2.

Durmaz, S. et al. "Phase Separation during the Formation of Poly(acrylamide) Hydrogels" Polymer 41, 2000, pp. 5729-5735.

Gong, J.P. et al. "Friction of Polymer Gels and the Potential Application as Artificial Cartilage." SPIE, Mar. 1999, pp. 218-225, vol. 3669.

Guilherme, R. et al. "Hydrogels based on PAAm network with PNIPAAm included: hydrophilic-hydrophobic transition measured by the partition of Organe II and Methylene Blue in Water." Polymer 44, 2003, pp. 4213-4219.

Hassan, C.M. et al. "Modeling of Crystal Dissolution of Poly(vinyl alcohol) gels produced by freezing/thawing processes." Polymer 41, 2000, pp. 6729-6739.

Hassan, C.M. et al. "Structure and Morphology of Freeze/Thawed PVA Hydrogels," Macromolecules, 2000, pp. 2472-2479, vol. 33, No. 7.

Hickey, A.S. et al. "Solute Diffusion in Poly(vinyl) alcohol/poly(acrylic) acid composite membranes prepared by freezing/thawing techniques." J. Memb. Sci. 107, 1995, pp. 229-237.

Kobayashi, M. et al. "Development of an Artificial Meniscus Using Polyvinyl alcohol-hydrogel for early return to, and continuance of, athletic life in sportspersons with severe meniscus injury." Abstract only, The Knee 10, 2003, p. 53.

Kobayashi, M. et al. "Preliminary Study of Polyvinylalcohol-hydrogel (PVA-H) artificial meniscus." Biomaterials 24, 2003, pp. 639-647.

Lester, C.L. et al. "Physical Properties of Hydrogels Synthesized from Lyotropic Liquid Crystalline Templates" Chem. Mater. 15, 2003, pp. 3376-3384.

Mano, V. et al. "Blends Composed of Poly(N-Isopropylacrylamide) and an Ethylene/Vinyl Alcohol Copolymer: Thermal and Morphological Studies" J. App. Polymer Sci., 2004, pp. 501-505.

Park, J.H. et al. "Hydrogels based on Poly(ethylene oxide) and poly (tetramethylene oxide) or poly)dimethyl siloxane). III. In vivo Biocompatability and Biostability." J. Biomed. Mater. Res. 64A, 2003, pp. 309-319.

Schmedlen, R.H. et al. "Photocrosslinkable polyvinyl alcohol hydrogels that can be modified with cell adhesion peptides for use in tissue engineering." Biomaterials, 23, 2002, pp. 4325-4332.

Suggs, L.J. et al. "In vitro Cytotoxicity and In Vivo Biocompatability of Poly(propylene fumurate-co-ethylene glycol) hydrogels." J. Biomed. Mater. Res., 1999, pp. 22-32, vol. 46.

Thomas, J.D. "Novel Associated PVA/PVDP Hydrogels for Nucleuc Pulposus Replacement." Thesis, Master of Science in Material Engineering Degree, Drexel University, Sep. 2001.

Ushio, K. et al. "Attachment of Artificial Cartilage to Underlying Bone." J. Biomed. Mater. Res. Part B: Appl. Biomater. 68B, 2004, pp. 59-68.

Ushio, K. et al. "Partial Hemiarthroplasty for the treatment of Osteonecrosis of the Femoral Head: An Experimental Study in the Dog." J. Bone Joint Surg., 2003, pp. 922-930, vol. 85B.

Zhang, X. et al. "Synthesis and Characterization of Partially Biodegradable, Temperature and pH Sensitive Dex-MA/PNIPAAm Hydrogels." Biomat., 25, 2004, pp. 4719-4730.

"Lecture 7: Hydrogel Biomaterials: Structure and Physical Chemistry," Spring 2003, 8 pages.

ISR/WO for PCT/US2006/006356 dated Jun. 22, 2006, 9 pages.

European Patent Office, Invitation to Pay Additional Fees received in corresponding PCT Application No. PCT/US2006/046725 dated Apr. 22, 2008, 8pp.

C.M. Hassan et al., Diffusional Characteristics of freeze/thawed poly(vinyl alcohol) hydrogels: Applications to protein controlled release from multilaminate devices, European Journal of Pharmaceutics and Biopharmaceutics, 2000, pp. 161-165, vol. 49.

K. R. Park et al., Synthesis of PVA/PVP hydrogels having two-layer by radiation and their physical properties, Radiation Physics and Chemistry, Jun. 2003, p. 361-365, vol. 67 No. 3-4, Elsevier Science Publishers BV, Amsterdam NL.

L. S. Bass et al., Laser Tissue Welding: A Comprehensive Review of Current and Future Clinical Applications, Lasers in Surgery and Medicine, 1995, p. 315-349, vol. 17, Wiley-Liss, Inc., New York, US.

EP Search Report for EP Application No. 1115 5892 dated May 27, 2011.

European Patent Office, International Search Report and Written Opinion for corresponding PCT Application No. PCT/US2006/046725 dated Jul. 28, 2008; 20 pp.

Bray, J.C. et al. "Poly(vinyl Alcohool) Hydrogels: Formation by Eelctron Beam Irradiation of Aqueous Solutions and Subsequent Crystallization." J. Applied Polymer Sci., vol. 17, pp. 3779-3794, 1973.

Bray, J.C. et al. "Poly(vinyl Alcohol) Hydrogels for Synthetic Articular Cartilage Material," Biomed. Mater. Res., vol. 7, pp. 431-443, 1973.

Kawanishi, K. Thermodynamic Consideration of the Sol-Gel Transition in Polymer Solutions. 35th Annual Meeting of the Society of Polymer Science, Japan 1986.

Lozinsky, V.I. et al. "Study of Cryostructures of Polymer Systems, XIV. Poly(vinyl alchohol) Cryogels: Apparent Yield of Freeze-Thaw Induced Gelation of Concentrated Aqueous Solutions of the Polymer." J. Applied Polymer Sci., vol. 77, 1822,1831 (2000).

Lozinsky, V.I. et al. "Study of Cryostructuration of Polymer Systems, XVII. Poly(vinyl alcohol) Cryogels: Dynamics of the Cryotropic Gel Formation." J. Appl. Polymer Sci., vol. 77, 2017-2023 (2000).

Lozinsky, V.I. et al. "Swelling Behavior of poly (vinyl alcohol) cryogels employed as matrices for cell immobilization." Enzyme Microb. Technol., vol. 18.

Peppas et al. "Reinforced Uncrosslinkable Poly (vinyl alcohol) gels produced by cyclic freezing-thawing processes: A Short Review." J. Controlled Release, 16 (1991), 305-310.

Mondino, A.V. et al. "Physical properties of gamma irradiated poly (vinyl alcohol) hydrogel preparations" Radiation Physics and chemistry, 55, p. 723,726 (1999).

Urushizaki, F. Swelling and Mechanical Properties of Poly (vinyl alcohol) Hydrogels. Intl. J. Pharma., 58, 135-142, 1990.

Lozinsky, V.I. "On the Possibility of Mechanodestruction of Poly (vinyl Alcohol) Molecules under Moderate Freezing of its Concentrated Water Solutions." Polymer Bulletin, 15, p. 333-340 (1986).

Yokoyama, F. "Morphology and Structure of Highly Elastic Poly (vinyl alcohol) Hydrogel Prepared by Repeated Freezing-and-Melting" Colloid & Polymer Sci. 264, 595-601 (1986).

Covert, R.J. et al. "Friction and Wear Testing of a New Biomaterial for Use as an Articular Cartilage Substitute," BED 50 (2001), 355-356, Bioengineering Conference, ASME 2001.

Ding, Mei Yee. Characterisation of Polyvinyl Alcohol Hydrogels, 2003. Undergraduate Chemical Engineering Thesis, University of Queensland, Brisbane QLD 4072, Australia http://www.cheque.uq.edu.au/ugrad/theses/2003/pdf/CHEE4006/40054522/40054522.pdf (working link on Apr. 20, 1009).

Jaguar-Grodzinski, J. "Biomedical Application of Functional Polymers." Reactive and Functional Polymers 39 (1999) 99-138.

Ulanski, P. et al. "OH-Radical induced crosslinking and strand breakage of poly (vinyl alcohol) in aqueous solution in the absence and presence of oxygen. A pulse radiolysis and product study" Macromol. Chem. Phys. 195, p. 1443-14461 (1994).

EP Search Report for EP06255568.5, Jun. 15, 2007.

Rao et al. J. Chem. Soc. Dalton Trans., 2001, 1939-1944.

Li et al. Anal. Biochem., 256, 130-132 (1998).

Anseth et al. "In situ forming degradable networks and their application in tissue engineering and drug delivery." J. Controlled Release 78 (2002), 199-209, 2002.

Lin-Gibson et al. "Synthesis and Characterization of PEG Dimethacrylates and Their Hydrogels." Biomacromolecules 2004, 5, 1280-1287, 2004.

Peppas et al. Structure and Applications of Poly(vinyl alcohol) Hydrogels Produced by Conventional Crosslinking or b Freezing/Thawing Methods. Adv. Polymer Sci. 153, 37 (2000).

LeGeros R. Z., "Calcium phosphates in oral biology and medicine," Monograph in Oral Science, vol. 15, pp. 1-201.

Chow et al.,"Octacalcium Phosphate," Monograph in Oral Science, vol. 18, pp. 94-112 and 130-148.

Carey et al., Adv. Org. Chem., Part B., p. 892, 2001.

Hassan et al. "Cellular PVA Hydrogels Produced by Freeze/Thawing." J. Appl. Poly. Sci. 76, 2075 (2000).

Moro et. al. "Surface Grafting of Artificial Joints with Biocompatible Polymer for Preventing Periprosthetic Osteolysis." Nature Materials, 3, 829 (2004).

Hickey et al. :Solute Diffusion in Poly(vinyl)alchohol/poly(acrylic acid) composite membranes prepared by freezing/thawing techniques. Polymer 38, pp. 5931-5936 (1997).

Wang B., et al. The Influence of Polymer concentration on the Radiation-chemical Yield of Intermolecular Crosslinking of Poly(Vinyl Alcohol) by gamma-rays in Deoxygenated Aqueous Solution. Radiation Physics and Chemistry, 2000. 59: p. 91-95.

Rosiak, J. M. & Ulanski, P. Synthesis of hydrogels by irradiation of polymers in aqueous solution, Radiation Physics and Chemistry 1999 55: 139-151.

Stammen, J. A., et al. Mechanical properties of a novel PVA hydrogel in shear and unconfined compression Biomaterials, 2001 22: p. 799-806.

Yamaura, K., et al. Properties of gels obtained by freezing/thawing of poly(vinyl alcohol)/water/dimethyl sulfoxide solutions. Journal of Applied Polymer Science 1989 37:2709-2718.

Lozinsky, V. I. and Damshkaln, L. G. Study of cryostructuration of polymer systems. XVII. Poly(vinyl alcohol) cryogels: Dynamics of cryotropic gel formation. Journal of Applied Polymer Science 2000 77:2017-2023.

Oka M et al. "Development of artificial articular cartilage," Pro. Inst. Mech. Eng. 2000 214:59-68.

EP Search Report for EP 06256525.4 dated May 20, 2007.

Babb et al. "Perfluorcyclobutane Aromatic Ether Polymers. III. Synthesis and . . . " J. Applied. Polymer Sci., vol. 69, (1998), pp. 2005-2012.

Glossary of Basic Terms in Polymer Science published by IUPAC, Pure Appl. Chem., 68, 2287-2311 (1996).

EP Search Report for EP06256452.1 dated May 23, 2007.

ISR/WO for PCT/US2006/046725 dated Jul. 28, 2008.

ISR/WO for PCT/EP2005/010931 dated Feb. 16, 2006.

ISR/WO for PCT/US2007/064782 dated May 3, 2008.

Search Report for PCT/US2008/071435 dated Feb. 2, 2009.

\* cited by examiner

METHODS OF BONDING OR MODIFYING HYDROGELS USING IRRADIATION

RELATED APPLICATION

This application claims priority to U.S. Provisional Patent Application Ser. No. 60/748,293 filed Dec. 7, 2005, now pending and expressly incorporated by reference herein in its entirety.

FIELD OF THE INVENTION

The present invention provides methods and processes to attach or bond hydrogels to suitable materials, such as soft tissues, elastomers, and hydrogel surfaces, using irradiation techniques. This invention also provides methods and processes to modify hydrogel articles by creating crosslinked regions in these hydrogels using these irradiation techniques. Specifically, lasers that are tuned to the absorption bands of chemical groups may be used to attach or bond hydrogels to suitable materials such as soft tissues, elastomers, and hydrogels, to create crosslinked regions, or to modify hydrogel articles.

BACKGROUND

Hydrogels are water-swellable or water-swollen materials whose structure is typically defined by a crosslinked or interpenetrating network of hydrophilic homopolymers or copolymers. The hydrophilic homopolymers or copolymers can be water-soluble in free form, but in a hydrogel they may be rendered insoluble generally due to the presence of covalent, ionic, or physical crosslinks. In the case of physical crosslinking, the linkages can take the form of entanglements, crystallites, or hydrogen-bonded structures. The crosslinks in a hydrogel provide structure and physical integrity to the polymeric network.

Hydrogels can be classified as amorphous, semicrystalline, hydrogen-bonded structures, supermolecular structures, or hydrocolloidal aggregates. Numerous parameters affect the physical properties of a hydrogel, including porosity, pore size, nature of gel polymer, molecular weight of gel polymer, and crosslinking density. The crosslinking density influences the hydrogel's macroscopic properties, such as volumetric equilibrium swelling ratio, compressive modulus, or mesh size. Pore size and shape, pore density, and other factors can impact the surface properties, optical properties, and mechanical properties of a hydrogel.

Hydrogels can attain a wide variety of mechanical properties. In general, however, hydrogels are observed to be pliable or rubbery, with a lubricious surface. Hydrogels are generally characterized by a low coefficient of friction owing to the water content and water release properties at the surface. Frictional behaviors of hydrogels do not conform to Amonton's law, which states that the friction force is proportional to normal (i.e., orthogonal to the plane of motion) force. Unique load dependencies are observed for the friction coefficient of hydrogels: as load increases, friction coefficient decreases. As the hydrogel deforms under load, part of the water is squeezed out from the bulk gel and serves as a lubricant, leading to boundary lubrication or hydrodynamic lubrication.

Hydrogels have been fabricated from a variety of hydrophilic polymers and copolymers. Poly(vinyl alcohol), poly(ethylene glycol), poly(vinyl pyrrolidone), polyacrylamide, and poly(hydroxyethyl methacrylate), and copolymers of the foregoing, are examples of polymers from which hydrogels have been made.

Hydrogels can be neutral or ionic based on the type of charges of any pendent groups on the polymer chains. Hydrogels may exhibit swelling behavior that is dependent on and responsive to the external environment. Environmentally or physiologically responsive hydrogels, sometimes referred to as "intelligent" hydrogels, can exhibit drastic changes in swelling ratio due to changes in the external pH, temperature, ionic strength, nature of the swelling agent, and exposure to electromagnetic radiation. Hydrogels that exhibit pH dependent swelling behavior generally contain either acidic or basic pendant groups. In aqueous media of appropriate pH and ionic strength, the pendent groups can ionize, resulting in fixed charges on the gel.

Over the past three to four decades, hydrogels have shown promise for biomedical and pharmaceutical applications, mainly due to their high water content and rubbery or pliable nature, which can mimic natural tissue. Biocompatible hydrogels can be engineered to be either degradable or resistant to degradation. An additional advantage of hydrogels, which has only recently been appreciated, is that they may provide desirable protection of drugs, peptides, and especially proteins from the potentially harsh environment in the vicinity of a release site. Thus, such hydrogels could be used as carriers for the delivery of proteins or peptides by a variety of means, including oral, rectal, or in situ placement. Transport of eluents either through or from a hydrogel is affected by pore size and shape, pore density, nature of polymer, degree of hydration, and other factors. Hydrogels can also act as transport barriers, due to a size exclusion phenomenon. Also relevant in drug delivery applications are pH and ionic strength sensitivity, as exhibited by hydrogels of some ionic or ionizable polymers.

Hydrogels have been used and proposed for a wide variety of biomedical and drug delivery applications. For example, hydrogels have been utilized in controlled-release devices to achieve delivery of a drug or protein over time, and hydrogels have been widely employed in the fabrication of contact lenses. Hydrogels can be made to have properties similar to cartilage and are one of the most promising materials for meniscus and articular cartilage replacement. An overview of considerations for biological and medical applications of hydrogels can be found in Peppas, et al., Ann. Rev. Biomed. Eng. 2, 9 (2000), which is incorporated by reference in its entirety.

SUMMARY OF THE INVENTION

In one embodiment, the present invention provides a method of bonding a hydrogel component to a suitable surface or material, particularly a soft tissue surface, elastomer, or a hydrogel surface. This method includes contacting the surface, such as a soft tissue surface elastomer, or a hydrogel surface, with a hydrogel component, followed by irradiating a region at an interface of the hydrogel component and the surface to covalently bond the hydrogel component to the surface. This method, for example, is suitable for implanting a hydrogel component at a variety of soft tissue sites and is particularly suitable for implanting a hydrogel component at a collagen site or a joint site where the soft tissue surface is adjacent to an articulating or bearing surface. This bonding method may provide a desired gap free interface between the surfaces of the hydrogel and the soft tissue. In embodiments of this invention, the hydrogel component may be, or may include preformed hydrogels and hydrogel precursors, such as lyogels, that take in or incorporate water in the component after the hydrogel precursor is bonded to the surface. Owing to the thermoplastic character of certain hydrogel blends, the hydrogel component may also be in a flowable form.

In another embodiment, the invention provides a method of making a modified hydrogel article that includes attaching a hydrogel precursor or a hydrogel article to another surface, such as a soft tissue site, elastomer, or a hydrogel component, by irradiating a region at an interface of the hydrogel precursor or the hydrogel article and the surface to bond the hydrogel to the surface, and selectively irradiating predetermined regions of the hydrogel precursor or the hydrogel article to provide a greater concentration of crosslinking in the predetermined, irradiated regions. In the case when a hydrogel is bonded to another hydrogel, the result is a multilayered hydrogel article or a hydrogel article comprising multiple lamina.

In another embodiment, the invention provides a method of making a gradient in a hydrogel article by selectively irradiating predetermined regions in successive laminea of the hydrogel article to provide a greater concentration of crosslinking in the irradiated regions. The use of a laser as a suitable radiation source allows considerable flexibility in creating or generating crosslinking patterns that may be tailored to provide customized or intricate reinforcement schemes in the hydrogel article.

DETAILED DESCRIPTION

Irradiation Sources

Figure 1:
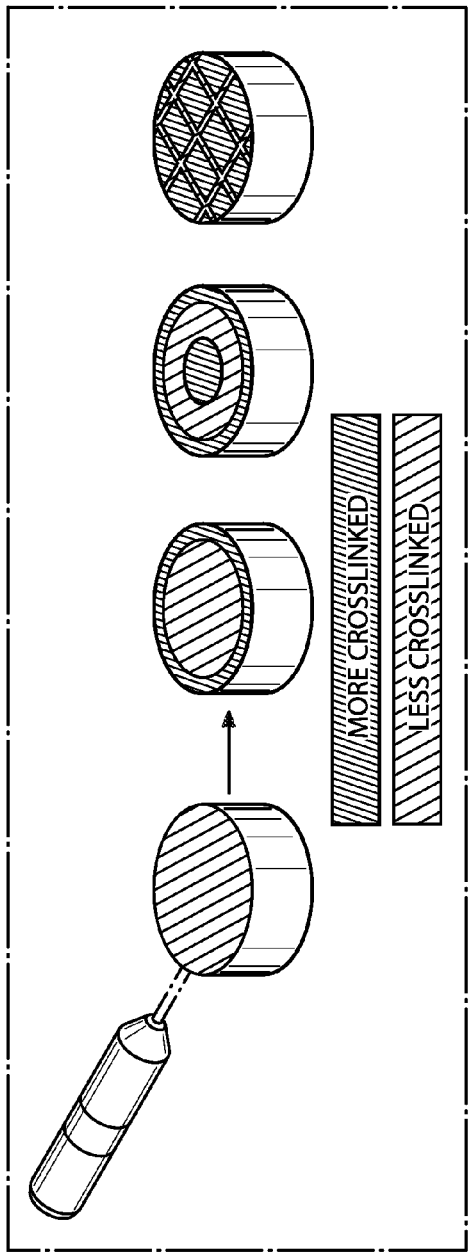
FIG. 1 shows a pictorial representation of a method of creating various gradients in a hydrogel article.

Irradiation of hydrogels results in a chemical crosslinking of the polymer chains by the formation of covalent bonds. Crosslinking is a process by which individual polymer chains are irreversibly linked together and can be due to either covalent bonding by irradiation or chemical bonding using reagents. Reversible physical bonding forces or interactions may also occur in the hydrogels in combination with chemical crosslinking. Specifically, for irradiation crosslinking, according to one embodiment, lasers that are tuned to the absorption bands of polymeric hydroxyl or carboxylic acid groups may be used to attach or bond hydrogels to suitable materials such as soft tissues and hydrogel surfaces, to create crosslinked regions, or to modify hydrogel articles. The use of irradiation to form covalent crosslinks has advantages over crosslinking by chemical reagents, such as increased control over the reaction, including the specific location of the reaction, and the absence of residue from the reagents, which can decrease the biocompatibility of the hydrogel.

Laser light in the near-infrared spectral region has unique properties that make it attractive as a source of thermal energy for attaching or bonding hydrogels to surfaces such as soft tissues and other hydrogel articles or for modifying a hydrogel article. Laser light has a high degree of brightness and directionality as compared to other light sources. This means that tighter focal spots may be created with higher positioning accuracy using laser light than light from other sources. It is desirable to operate with a single source of intense light that may be tuned over the near-infrared spectral region from about 800 nm to about 3000 nm. Suitable irradiation sources are lasers based on the active ions in host matrices, solid state, semiconductor lasers, pump diode lasers, and fiber lasers. Suitable ions for host matrices include $Er^{3+}$, $Cr^{4+}$, $Dy^{3+}$, $Nd^{3+}$, $Pr^{3+}$, $Ho^{3+}$, or $Tm^{3+}$. Suitable semiconductor lasers include InGaAs, InGaAlAs, and InGaAsP alloy semiconductor lasers, and AlGaAs quantum well (QW) intraband transition semiconductor lasers. Suitable fiber lasers include Yb (Ytterbium) doped fiber lasers and Er (Erbium) doped fiber lasers. Additional laser sources may include gas lasers such as HeNe, Argon, Krypton, and Fluorine. These lasers may be tuned to a spectral range that corresponds to the absorption bands of the desired functional group such as those of polymeric hydroxyl, hydroxyl, amine, sulfonic acid, sulfinic acid, phosphinic acid, phosphonic acid, amino, alcohol, nitrile, nitro, sulfide, sulfoxide, sulfone, thio, aldehyde, ketone, ester, carboxylic acid groups or water, permitting the attaching or bonding of hydrogels to soft tissues without additional tissue solders, UV initiators, or dyes, or to another hydrogel surface.

The present invention is based, in part, on the premise that the choice of light source utilized in irradiation-based attaching or bonding procedures, such as hydrogel-tissue bonding, play a role in the effectiveness of the technique to achieve practical hydrogel-tissue bonds. The interaction of the hydrogel or soft tissue with light is governed by the optical parameters of the hydrogel or tissue, including scatter and absorption, which in turn are dependent on the wavelength of the incident light. Under proper circumstances, light energy that is converted to heat in the hydrogel or tissue will cause bonding of hydrogels to adjacent hydrogels and/or tissues as well as other components, such as collagen, thereby achieving the desired attachment or bond. This process may be refined using the appropriate light source, focal length, pulse width, non-pulsed source, and delivery system best matched to the particular hydrogels and soft tissues at the site.

There are a variety of types of soft tissue in the body that differ in their optical properties, such as absorption, scatter and reflectivity. The interaction of a particular hydrogel or tissue with the incident radiation is significant in the effectiveness of the hydrogel-tissue bonding operation. It may be desirable to have a broad band light source that can be modified to suit the particular type and thickness of the hydrogel or tissue to be treated. In particular, light in the near-infrared spectral region that coincides with a resonance in the absorption spectrum of hydroxyl or carboxylic acid groups in the hydrogel or water in the tissue has been identified as being convenient for the hydrogel-tissue bonding process. Since water makes up a significant percentage of living tissues, it therefore has an important role in the absorption properties of tissue. The variation in the penetration depth is a function of the change in water absorption maximum to minimum over the tuning range of the light source.

By implementing a light source that is tunable over the spectral region of hydroxyl groups, carboxylic acid groups or water absorption, the depth to which the incident light can penetrate a tissue can be selected. The 900-2000 nm wavelength range is particularly attractive for hydrogel-tissue bonding applications as a large change in energy absorption is experienced in this region. Strong absorption in the 1400 nm region, such as in the 1430 to 1470 nm region, has a tissue penetration depth of about 0.1 mm while light at 1300 nm may penetrate more deeply to about 5 mm into the tissue. This large degree of penetration depths makes it feasible to optimize the attachment and bonding process for a wide variety of tissue types. Suitable wavelengths for hydroxyl containing polymers are between 1280-1400 nm. Cunyite and Fosterite lasers are suitable sources for hydroxyl polymers. For those polymers containing CO bonds, the suitable wavelength range is generally between 1450-1600 nm.

In addition, by utilizing the appropriate wavelength, the absorption and scattering properties of the tissue can be exploited to yield a strong bond of the hydrogel to the soft tissue. For instance, light of a wavelength that is strongly absorbed by the tissue is preferable because a large percentage of the light will be absorbed in the tissue in the bonding region making the process more efficient, and minimizing the light absorbed in other regions, thereby reducing any unintended injury to underlying tissue. Light in the near-infrared spectral region is especially desirable for this operation because the wavelengths in this region may be tuned continuously over a range of penetration depths in tissue from about 0.1 mm to about 5 mm.

In some embodiments, tunable near-infrared lasers based upon the $Cr^{4+}$-active ion, such as Cr:forsterite lasers with wavelengths tunable from about 1150 to about 1350 nm, Cunyite $Cr:Ca_2GeO_4$ lasers tunable from about 1350 to about 1500 nm, or $Cr^{4+}$ YAG lasers tunable from about 1370 to about 1600 nm (which have been used for tissue welding processes) are used. The unique tuning ranges of these lasers make them attractive as irradiation sources for the hydrogel-tissue bonding process because their simplicity of operation negates the need for the additional complexity of wavelength conversion processes that are required to generate light from other lasers. Moreover, bonding may be possible using the absorption bands of hydroxyl groups, carboxylic acid groups or water in the 1150 to 1600 nm spectral region without additional dyes. Examples of dyes include ADS 1075A (American Dye Source, Quebec, CA), ADS1060WS (American Dye Source), and ClearWeld® (Cambridge, UK). The tunable wavelengths from the $Cr^{4+}$ lasers also offer more versatility in selecting precise depth penetration for laser irradiation as the wavelength from this source is strongly absorbed by hydroxyl containing species including polymer hydroxyl groups and collagen.

The $Cr^{4+}$ lasers emit radiation in the near-infrared spectral range, where there is less scattering and deeper penetration than for visible light, such as Argon (1 to 2 mm) and other lasers, including Nd:YAG lasers (3 to 4 mm) and $CO_2$ laser (0.02 mm). These $Cr^{4+}$ laser beams have penetration depths varying from about 2 to about 5 mm depending on their wavelengths, which can heat water and adipose in the tissue to induce attachment and binding of hydrogels to the tissue. These $Cr^{4+}$ lasers may be suitable for thin-walled tissue, as well as for thick-walled tissue when the appropriate wavelength is chosen. Output of these tunable lasers has several key advantages over single-wavelength lasers. The irradiation can be tuned to the absorption bands of different tissue constituents, such as, the 1203 nm band for adipose, and the 1350 nm band for water. Different kinds of tissues can be treated by selecting different wavelengths. An additional advantage in the use of these lasers is utilizing quartz fiber optics to deliver the beams, which a medical practitioner can operate easily. The tunable wavelengths from the $Cr^{4+}$ lasers also offer more versatility in selecting precise depth penetration for hydrogel-tissue bonding.

Without being held to a single theory, one mechanism by which tissue to hydrogel bonding with a laser works may be that the laser beam first heats the tissue due to the absorption bands of water in the hydrogels and soft tissues. This heating facilitates the bonding of molecules in native tissue proteins, such as collagen, with the molecules of the hydrogels through bond breaking and reformation. In the case of hydrogel to hydrogel bonding, light energy that is converted to heat in the hydrogel will cause bonding of adjacent hydrogels, thereby achieving the desired attachment or bond. An example of this process is the laser induced thermal dehydration of the hydroxyl groups to produce ether linkages. This process may be refined using the appropriate light source and delivery system best matched to the particular hydrogels.

Crosslinking Hydrogels

In one embodiment of the invention, irradiation may be used to selectively crosslink regions of hydrogels in a variety of geometries, patterns or gradients. This selective crosslinking may be used to customize and tailor the mechanical and physical characteristics of a hydrogel article. A laser may be used to create a gradient in a shaped hydrogel article because there will be a greater concentration of the laser energy at the surface of the article and therefore a greater concentration of crosslinking in that region. In addition, a laser may be used to create specific crosslinked geometries in a hydrogel article using a rasterizing approach or process, as shown in FIG. 1. Rasterizing is a pattern of horizontal lines created by an electron beam, irradiation, laser, or other wavelength source to create an image or pattern. In this case, rasterizing creates a crosslink pattern in the desired article. This crosslinking process may be used either during production of the article itself or may be used in situ after the article is placed in contact with a soft tissue at a desired site or location, such as at a joint repair site of a hip, knee, spine, finger or shoulder. This crosslinking process may also be used on separate hydrogel components that are subsequently bonded together. When a laser is used to crosslink the hydrogel, there is no, or little, degradation of the molecular weight of the polymers and therefore no detrimental change to the mechanical and physical properties of the hydrogel article. The crosslinking provides reinforcement to the network and can create lower creep strain, higher tear resistance, and increased stiffness.

In another embodiment, the invention provides a method of making a crosslinked gradient or pattern in a hydrogel article comprising the step of selectively irradiating predetermined regions of the hydrogel article to provide a greater concentration of crosslinking in the irradiated region. In some embodiments the predetermined regions are a rasterized pattern. In other embodiments the predetermined regions are geometric patterns. In still other embodiments, the predetermined regions are a three dimensional pattern.

In another embodiment, the invention provides a method of making a multilayered hydrogel article. In this embodiment, a gradient or pattern is created utilizing a layering approach. In a first step, a layer of a hydrogel or a hydrogel precursor is irradiated in a predetermined pattern to provide a patterned first hydrogel layer. A second layer of the same or different hydrogel or hydrogel precursor is then contacted with the patterned first hydrogel layer to create a second hydrogel layer. This second hydrogel layer is then irradiated in a predetermined pattern that may be the same of different than the predetermined pattern that was used to irradiate the first layer. This process can be performed any number of times to provide a desired multilayered hydrogel article. The hydrogel layers are bonded to one another by irradiating the interface between them.

In another embodiment, a method of making a modified hydrogel article is provided that includes two steps: a first step of attaching a hydrogel article to a soft tissue site by irradiating a region at an interface of the hydrogel article and soft tissue to bond the hydrogel article to the soft tissue, and a second step of selectively irradiating predetermined regions of the hydrogel article to provide a greater concentration of crosslinking in the predetermined, irradiated regions. A variation of this process would be to combine these two steps with the layering process described above. This combination of processes would provide a process to construct a layered article at a tissue site where the mechanical properties and physical characteristics of the article are controlled by, for example, the crosslinking patterns that are created in each layer of the article.

Bonding Surfaces

A variety of surfaces are suitable for bonding of hydrogels, preformed hydrogel components, hydrogel precursors, lyogels or hydrogel articles using the methods and processes of the present invention.

In one embodiment, the surface may be a polymeric surface that will have appropriate chemical moieties in the structure of the polymer that will interact or bond with the hydroxyl groups or carboxylic acid groups of suitable hydrogels or hydrogel components. Appropriate chemical moieties include, but are not limited to hydroxyl, ether, ester, carboxylic acid, amine, amide, or silyl moieties. Other chemical moieties that are able to form covalent or other chemical bonds with hydroxyl or carboxylic acid groups are also suitable for use in the methods and processes of this invention.

Figure 2:
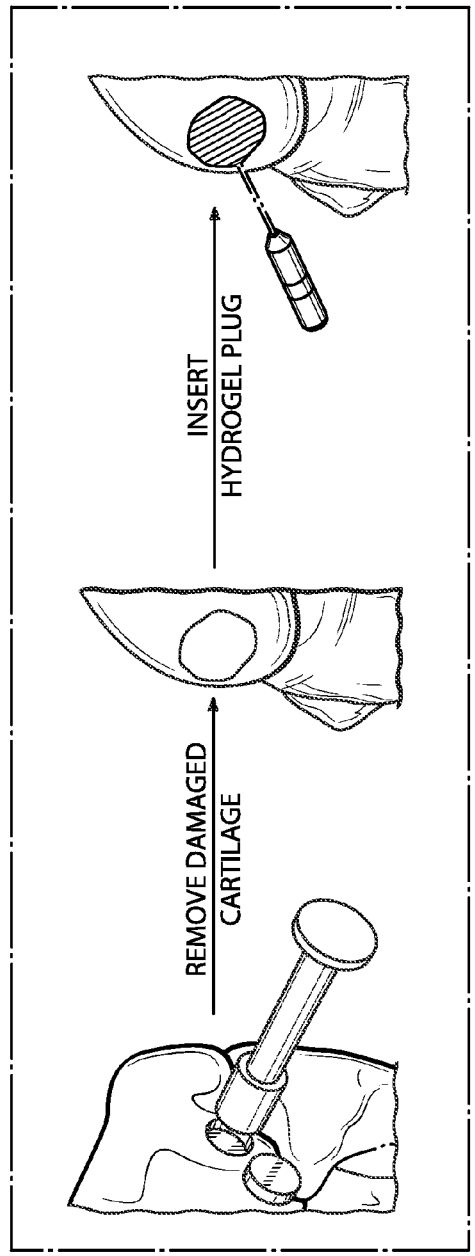
FIG. 2 shows a pictorial representation of a method of attaching a hydrogel component to a soft tissue.

In another embodiment of this invention, the surface may be a soft tissue. Soft tissue is a term that refers to structures of the body that connect, envelope, support and/or move the structures around it. Examples of soft tissue include muscle, tendons, ligaments, synovial tissue, fascia, which surrounds the musculoskeletal components, and other structures such as nerves, blood vessels and fat. In some embodiments, the soft tissue will be cartilage, meniscus or other soft tissue that is located at a joint site such as a hip, knee, spine, finger, elbow or shoulder joint, as shown schematically in FIG. 2.

Hydrogels

The water-swellable articles and hydrogels that may be used in the present invention typically include a hydrophilic polymer. In one embodiment, the hydrophilic polymer may be poly(vinyl alcohol)(PVA), or derivatives thereof. By way of illustration only, other hydrophilic polymers that may be suitable include poly(hydroxyethyl methacrylate), poly(vinyl pyrrolidone), poly(acrylamide), poly(acrylic acid), hydrolyzed poly(acrylonitrile), poly(ethyleneimine), ethoxylated poly(ethyleneimine), poly(allylamine), or poly(glycols) as well as blends or mixtures of any of these hydrophilic polymers.

In certain embodiments, at least one component of the hydrogel is PVA as the hydrophilic polymer. PVA for commercial use is generally produced by free-radical polymerization of vinyl acetate to form poly(vinyl acetate), followed by hydrolysis to yield PVA. The hydrolysis reaction does not go to completion, which leaves pendent acetate groups at some points along the polymer chain. In practice, PVA can therefore be considered, in part, a copolymer of vinyl acetate and vinyl alcohol. The extent of the hydrolysis reaction determines the degree of hydrolysis of the PVA. Commercially available PVA can have a degree of hydrolysis over 98% in some cases.

The degree of hydrolysis (which indicates the number of remaining pendent acetate groups) affects the solubility, chemical properties, and crystallizability of PVA. PVA having a very high degree of hydrolysis (greater than 95%) is actually less soluble in water than PVA having a lower degree of hydrolysis, due to the high degree of intra-chain hydrogen bonding by the hydroxyl groups. For PVA having a lower degree of hydrolysis, the residual acetate groups weaken the intramolecular and intermolecular hydrogen bonds and enable solvation by water.

Similarly, the presence of residual acetate groups also affects the crystallizability of PVA. PVA having a high degree of hydrolysis is more difficult to crystallize than PVA having a lower degree of hydrolysis. Crystalline PVA is reported to have a glass transition temperature of about 85° C., and melt in the range of 220° to 240° C. The presence of water or other solvents in crystalline PVA reportedly depresses the glass transition temperature significantly from that of pure PVA. See Peppas, et al., Adv. Polymer Sci. 153, 37 (2000).

Commercially available PVA is generally characterized by a fairly wide molecular weight distribution. A polydispersity index of 2 to 2.5 is common for commercial PVA, and a polydispersity index of up to 5 is not uncommon. The polydispersity index, or PDI, is a measure of the distribution of molecular weights in a given polymer sample. The molecular weight distribution of PVA affects properties such as crystallizability, adhesion, mechanical strength, and diffusivity.

For use in the present invention, the PVA is desired to have an average molecular weight above 50 kDa and a degree of hydrolysis above 70%. More commonly, the PVA has an average molecular weight above 80 kDa and a degree of hydrolysis above 90%. In one embodiment, the PVA is characterized by an average molecular weight in the range from about 86 kDa to 186 kDa.

In some embodiments of the present invention the hydrophilic polymer may be a hydrogel blend including PVA and a second polymer having hydrophobic recurring units and hydrophilic recurring units. The second polymer may be poly (ethylene-co-vinyl alcohol), for example. As non-limiting examples, other suitable polymers include diol-terminated poly(hexamethylene phthalate) and poly(styrene-co-allyl alcohol).

The blend may comprise from about 5% to about 95% by weight of the hydrophilic polymer, and about 5% to about 95% by weight of the second polymer. More suitably, the blend comprises from about 30% to about 95% by weight of the hydrophilic polymer, and about 5% to about 70% by weight of the second polymer. In some embodiments, the blend comprises from about 50% to about 95% by weight of the hydrophilic polymer, and about 5% to about 50% by weight of the second polymer.

In one embodiment, the blend may comprise from about 5% to about 95% by weight of PVA, and about 5% to about 95% by weight of poly(ethyleneco-vinyl alcohol). In another embodiment, the blend comprises from about 30% to about 95% by weight of PVA, and about 5% to about 70% by weight of poly(ethylene-co-vinyl alcohol).

In one embodiment, the blend comprises or consists essentially of about 5 to about 95% by weight of PVA and about 5 to about 95% by weight poly(styrene-co-allyl alcohol) as the second polymer. In another embodiment, the blend comprises or consists essentially of about 5 to about 95% by weight of PVA and about 5 to about 95% diol-terminated poly(hexamethylene phthalate) as the second polymer.

In certain embodiments, the second polymer has both hydrophobic and hydrophilic character. Generally, the second polymer will include hydrophobic recurring units and hydrophilic recurring units. The polymer can be a copolymer, for example. It may be possible to vary or adjust the "stiffness" of the water-swellable article or the hydrogel that results from hydration, by varying the overall hydrophobicity or hydrophilicity of the polymer. This may be due to a greater or lesser number of crosslinking sites.

In some embodiments, the hydrophobic recurring units comprise an aliphatic hydrocarbon segment. Aliphatic hydrocarbon recurring units may take the form —[$CH_2CH_2$—] or —[$CH_2CH(CH_3)$—], for example. In other embodiments, hydrophobic recurring units can comprise aliphatic, cyclic, or aromatic hydrocarbon pendent groups (e.g., pendant phenyl groups), or heterocyclic or heteroaromatic pendent groups.

By way of example only, the hydrophobic region can also comprise fluorocarbon segments, segments comprising cyano pendant groups, or segments comprising imide groups.

In one embodiment, a majority of the hydrophobic recurring units are of the form —[$CH_2CH_2$—]. As used herein, the term "majority" means at least 50%. In another embodiment, the hydrophobic recurring units are predominantly of the form —[$CH_2CH_2$—]. As used herein, the term "predominantly" means a high proportion, generally at least 90%.

The hydrophilic recurring units of the polymer include recurring units having hydrophilic groups, such as hydroxyl pendent groups, carboxylic acid or sulfonic acid pendent groups, hydrophilic heterocyclic groups such as pyrrolidone pendent groups, or alkylene oxide groups (e.g., ($C_1$-$C_6$) alkylene oxide groups, more typically ($C_1$-$C_3$) alkylene oxide groups, such as —[$CH_2O$—], —[$CH_2CH_2O$-1, —[$CH(CH3)O$⁻1, —$CH_2CH_2CH_2O$⁻1, ⁻[$CH(CH_3)CH_2O$-1, ⁻[$CH2CH(CH_3)O$—]) in the polymer backbone or as pendent groups.

In one embodiment, a majority of the hydrophilic recurring units comprise pendant hydroxyl (—OH) groups. In another embodiment, the hydrophilic recurring units predominantly comprise pendant —OH groups. In one embodiment, a majority of the hydrophilic recurring units are of the form —[CH2CH(OH)—]. In another embodiment, the hydrophilic recurring units predominantly are of the form —[CH2CH(OH)—].

A copolymer derived from a hydrophobic monomer and a hydrophilic monomer may be suitable as the polymer, for example. One suitable copolymer comprises recurring units of the form —[$CH_2CH_2$—] and recurring units of the form —[CH2CH(OH)—], for example. In one embodiment, the copolymer comprises recurring units of the form —[$CH_2CH_2$—] and recurring units of the form —[$CH_2CH$(OH)—] in a ratio in the range from about 1:1 to about 1:3.

An example of a copolymer is poly(ethylene-co-vinyl alcohol), also known as "EVAL", "PEVAL" or "EVOH." Poly(ethylene-co-vinyl alcohol) can be formed into a hard, crystalline solid and is used commercially in food packaging and other applications. Commercially available grades of poly(ethylene-co-vinyl alcohol) are suitable for use in preparing hydrogels. Commercially available grades are available having an ethylene content, expressed as a mole-percent, of 26%, 27%, 28%, 29%, 32%, 35%, 44%, and 48%.

Other copolymers having hydrophilic recurring units and hydrophobic recurring units that may be suitable include poly(ethylene-co-acrylic acid) and poly(ethylene-co-methacrylic acid). In one embodiment, the copolymer is poly(styrene-co-allyl alcohol) with an average molecular weight of 1600.

A block copolymer having hydrophobic blocks and hydrophilic blocks may also suitable as the polymer. For example, a block copolymer could be derived from oligomers or prepolymers having the hydrophobic and hydrophilic segments. A prepolymer is a polymer of relatively low molecular weight, usually intermediate between that of the monomer and the final polymer or resin, which may be mixed with compounding additives, and which is capable of being hardened by further polymerization during or after a forming process.

Hydrophobic polymers or oligomers with hydrophilic end groups may also be suitable as the second polymer in a copolymer embodiment. An example of a oligomer having hydrophilic end groups is diol-terminated poly(hexamethylene phthalate) with an average molecular weight of 1000.

By way of illustration only, other polymers with hydrophilic and hydrophobic character that may be used include dicarboxy-terminated poly(acrylonitrile-co-butadiene), poly (3,3',4,4'-biphenyltetracarboxylic dianhydride-co-1,4-phenylenediamine) amic acid, poly(3,3',4,4'-benzophenonetetracarboxylic dianhydride-co-4,4'-oxydianiline/1,3-phenylenediamine) amic acid, poly(bisphenol A-co-4-nitrophthalic anhydride-co-1,3-phenylenediamine), polybutadiene epoxy/hydroxyl functionalized, hydroxyl-terminated polybutadiene, poly(ethylene-co-1,2-butylene)diol, hydroxyl-terminated poly(hexafluoropropylene oxide), and glycidyl end-capped poly(bisphenol A-coepichlorohydrin).

Suitable water-swellable or hydrogel articles may include a hydrophilic polymer and perfluorocyclobutane crosslinking segments. By way of illustration only, that hydrophilic polymers that may be suitable include PVA, poly(hydroxyethyl methacrylate), poly(vinyl pyrrolidone), poly(acrylamide), poly(acrylic acid), hydrolyzed poly(acrylonitrile), poly(ethyleneimine), ethoxylated poly(ethyleneimine), poly(allylamine), and poly(glycols).

In one embodiment, a suitable water-swellable article includes hydrogel blends that include poly(vinyl alcohol) and a second polymer having hydrophobic recurring units and hydrophilic recurring units. In some embodiments, the water-swellable article is a thermoplastic.

The water-swellable article may also include additional polymers, peptides and proteins, such as collagen, or conventional additives such as plasticizers, components for inhibiting or reducing crack formation or propagation, components for inhibiting or reducing creep, or particulates or other additives for imparting radiopacity to the article. By way of example only, an additive for imparting radiopacity can include metal oxides, metal phosphates, and metal sulfates such as barium sulfate, barium titanate, zirconium oxide, ytterbium fluoride, barium phosphate, and ytterbium oxide.

The hydrophilic polymers reported above may be combined with crosslinked polymeric fibers in the presence of a suitable carrier. Suitable polymeric fibers include non-woven, short chopped fibers, which are commercially available from a variety of sources. Examples of suitable synthetic fibers include polyvinyl alcohol (PVA), polyethylene terephthalate (PET), poly imide (PI) and polyetheretherketone (PEEK). Suitable natural fibers may be formed from collagen, chitin, chitosan, and the like. Suitable biodegradable fibers include poly(glycolic acid) (PGA), poly(lactic acid) (PLA), poly(lactic-co-glycolide) (PLG) copolymers, poly(glycolide-colactide) (PGL) copolymers, polydioxanone, and the like. Suitable inorganic fibers include, for example, carbon fibers, ceramic fibers, hydroxyapatite, polysiloxane fibers, and the like. Commercially available PVA fibers, such as Kuralon® REC series available from Kuraray Co. Ltd. (Japan), are suitable for use in some embodiments and have an average diameter of 0.014-0.66 mm with an average length of 4-30 mm.

Prior to being combined with the hydrophilic polymer, the polymeric fibers may be crosslinked using irradiation or other conventional methods. In one embodiment, for example, the polymeric fibers may be gamma irradiated at 25 kGy prior to being combined with the hydrophilic polymer. In other embodiments, the polymeric fibers may be gamma irradiated at 50 kGy. Such crosslinking may improve the durability, preserve the crystallinity, and prevent dissolution of the fibers during subsequent processing steps, and in particular may prevent or reduce the breakdown of fibers in high temperature conditions.

In certain embodiments, the polymeric fibers are formed from the same polymer materials from which the hydrophilic polymer is derived. For example, both the hydrophilic polymer and the polymeric fibers may be formed or derived from poly(vinyl) alcohol.

Shaping Hydrogels

Processing methods to obtain a water-swellable article of desired shape or size may include solution casting, injection molding, or compression molding. In general, these methods may be used before or after crosslinking and/or bonding to a surface, as well as before or after the article is hydrated.

The hydrogels may be shaped into a variety of three dimensional forms such as cylindrical derivatives or segments, spherical derivatives or segments, or polyhedral derivatives or segments. Suitable hydrogel shapes may include at least one cylindrical, spherical or polyhedral segment. For example, suitable cylindrical derivatives or segments may include rod-shaped articles, rod-shaped articles with angled, pointed or curved ends, horse shoe, sausage or donut-like shaped articles, or other shapes that have some rounded portion. Further alternative shapes that are based on a spherical shape or on a polyhedral shape as well as complex shapes that may include combination cylindrical, spherical and/or polyhedral shapes are also within the scope of the present invention.

In some embodiments, the water-swellable article is thermoplastic in the form of a lyogel, which is a term generally used to described the physical state of a hydrogel material or article before the solvent used to prepare the hydrogel material is replaced with water. The thermoplastic lyogel can be melted and resolidified without losing its water-swellable properties. The thermoplastic quality of the water-swellable article as a lyogel allows for easy processability and end use. Upon melting, the lyogel becomes flowable and can therefore be extruded, injected, shaped, or molded.

To prepare a solution for use in casting, the appropriate polymers (and optionally any additives) are dissolved in the solvent. Heating the solvent may assist in dissolution of the polymers. The polymer-to-solvent ratio can vary widely. PVA hydrogels, by way of illustration, have reportedly been prepared using a polymer concentration of 2 to 50% by weight. In one embodiment of the method, the solution comprises about 0.5 parts of the polymer blend per one part solvent, by weight.

To prepare a material for compression or injection molding, the appropriate polymers (and optionally any additives) can be compounded in a heated mixing device such as a twin-screw compounder with the appropriate diluent or plasticizer. Heating the mixing device may assist in processing. Suitable temperatures depend on diluent or plasticizer and the chosen polymer system. The polymer-to-diluent ratio can vary widely. In one embodiment of the method, the blended hydrogel material comprises about 0.5 parts of polymer blend per one part solvent, by weight.

In Vivo Delivery of Thermoplastic Water-Swellable Material

As discussed above, some of the embodiments of the water-swellable and hydrogel articles in the lyogel state are thermoplastic and can be melted and re-solidified while retaining their water-swellable property or character. The thermoplastic property of the water-swellable material before the solvent is replaced with water allows for easy processability. Upon melting, the material becomes flowable and can be extruded, shaped, or molded to a desired configuration.

It has been observed that in some embodiments, the water-swellable material is also characterized by either low heat capacity or poor thermal conductivity, and can be manually handled in a heated, flowable state without special precautions. Melt-processability allows the water-swellable material to be manipulated so that in situ delivery and shaping can be accomplished. Therefore, the thermoplastic water-swellable material may be directly injected into the body of a patient, to allow for in situ shaping of a lyogel material that may then be attached or bonded at the site of injection according to the methods of the present invention. Such a technique may have practical application in several minimally invasive surgical procedures, as further described below.

In another embodiment, the invention provides for the use of a thermoplastic water-swellable material in conjunction with a step for heating and a step for in vivo delivery. The heating step can be any conventional heat source that would permit the water-swellable material to be heated to a temperature at which it can flow. An example of a suitable means for heating is a hot gun. The in vivo delivery step can be by means of any suitable device, such as a delivery tube or a needle. In some embodiments, the means for heating and means for delivery can be combined into one physical device. By way of example, a heated delivery tube could serve to provide both functions.

In Vivo Use of Water-Swellable Articles and Hydrogels

Hydrogels, including PVA hydrogels, have been used or proposed for use in a number of biomedical applications including cartilage replacement or augmentation and spinal disc replacement, augmentation, or rehabilitation.

The hydrogels possess a unique set of mechanical properties. In certain embodiments, such as the blended hydrogel described above, these materials exhibit toughness comparable or superior to other hydrogels including PVA-based hydrogels, while maintaining flexibility and a low elastic modulus. Examples of these improved properties are increased tensile strength, increased shear resistance, and improved elasticity. Furthermore, the properties of the blended hydrogels can be tailored to meet the requirements for a specific usage.

The blended hydrogels may also be highly hydrated, and exhibit higher strength and tear resistance compared to typical PVA hydrogels in some embodiments. These hydrogels can be engineered to exhibit tissue-like structure and properties. For example, these hydrogels may be engineered to substantially increase the elongation to failure characteristic of the material to provide an increased toughness of the material.

These hydrogels can therefore be suitably used in biomedical applications. Where the water-swellable hydrogel material is a thermoplastic, the advantage of in situ formability can be put to use as described above. For such an application, the water-swellable material can be hydrated in vivo after delivery and formation, to provide a hydrogel. For applications where the water-swellable material can be formed to shape externally, the water-swellable material can be hydrated either in vivo or ex vivo/in vitro.

One consideration for biomedical applications is that the material should be generally free of undesired materials that could cause an adverse reaction in the body, such as solvents, uncrosslinked polymer strands, and crosslinking agents, for example. The water-swellable materials and hydrogels of the present invention can be processed to remove the undesirable components. Further, the water-swellable materials and hydrogels can include inhibitors to counteract adverse reactions to the presence of any solvents, etc.

Hydrogel materials can be used in a variety of applications, including minimally invasive surgical procedures, as known in the field. By way of example, the hydrogels can be used to provide artificial articular cartilage as described, e.g., by Noguchi, et al., J. Appl. Biomat. 2, 101 (1991). The hydrogels can also be employed as artificial meniscus or articular bearing components. The hydrogels can also be employed in temporomandibular joints, in proximal interphalangeal joints, in metacarpophalangeal joints, in metatarsalphalanx joints, or in hip capsule joint repairs.

The water-swellable material or hydrogel of the invention can also be used to replace or rehabilitate the nucleus pulposus of an intervertebral disc. Degenerative disc disease in the lumbar spine is marked by a dehydration of the intervertebral disc and loss of biomechanical function of the spinal unit. A recent approach has been to replace only the central portion of the disc, called the nucleus pulposus. The approach entails a less invasive posterior surgery, and can be done rather rapidly. Bao and Higham developed a PVA hydrogel suitable for nucleus pulposus replacement, as described in U.S. Pat. No. 5,047,055. The hydrogel material, containing about 70% water, acts similarly to the native nucleus, in that it absorbs and releases water depending on the applied load.

The hydrogels can be similarly employed in the manner described therein, or in other applications known in the field. The water-swellable materials of the invention can also be employed in a replacement method. Where the water-swellable material is a thermoplastic, the advantage of in situ formability can be put to use as described above. For such an application, the water-swellable article in the form of a lyogel may be hydrated by a known solvent exchange process in vivo after delivery and formation, to provide a hydrogel.

The hydrogels can also be employed in a spinal disc prosthesis used to replace a part or all of a natural human spinal disc. By way of example, a spinal disc prosthesis may comprise a flexible nucleus, a flexible braided fiber annulus, and end-plates. The hydrogel may be employed in the flexible nucleus, for example. A spinal disc prosthesis is described in U.S. Pat. No. 6,733,533 to Lozier, for instance.

The ability of hydrogels to release therapeutic drugs or other active agents has been reported. The hydrogels can be suitably employed in vivo to provide elution of a protein, drug, or other pharmacological agent impregnated in the hydrogel or provided on the surface of the hydrogel.

Various embodiments of hydrogel blends that may be used in the present invention are set out in the following examples.

BLEND SYNTHESIS EXAMPLE 1

To a 2000 mL beaker equipped with a mechanical stirrer was added 100 g poly(vinyl alcohol), 100 g poly(ethylene-co-vinyl alcohol), and 1100 mL of DMSO. The poly(vinyl alcohol) is 99+% hydrolyzed with a weight average molecular weight (Mw) of 124 kDa to 186 kDa and was used as received from Sigma-Aldrich (St. Louis, Mo.). The poly(ethylene-co-vinyl alcohol) was used as received from Sigma-Aldrich and contains 44 mole-percent ethylene. The DMSO was used as received from Sigma-Aldrich and contains <0.4% water. The solution was heated to 90° C. for three hours.

After three hours, the solution was poured into a 9"×13" PYREX dish heated to 80° C. The solution was allowed to cool slowly to room temperature, and the dish was then placed into a freezer at −30° C. for three hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

BLEND SYNTHESIS EXAMPLE 2

To a 2000 ml, beaker equipped with a mechanical stirrer was added 100 g diolterminated poly(hexamethylene phthalate), 100 g poly(vinyl alcohol), and 1100 mL of DMSO. The poly(vinyl alcohol) is 99+% hydrolyzed, with a weight average molecular weight of 124 kDa to 186 kDa and was used as received from Sigma-Aldrich. The diol-terminated poly(hexamethylene phthalate), with a weight average molecular weight of 1000 Da, was used as received from Sigma-Aldrich. The DMSO was used as received from Sigma-Aldrich and contains ≦0.4% water. The solution was heated to 90° C. for 1.5 hours.

After 1.5 hours, the solution was poured into a 9"×13" PYREX dish, covered, and placed in a 60° C. oven for 12 hours. The dish was then placed into a freezer at −30° C. for three hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

BLEND SYNTHESIS EXAMPLE 3

To a 2000 ml, beaker equipped with a mechanical stirrer was added 100 g poly(styrene-co-allyl alcohol), 100 g poly(vinyl alcohol), and 1100 mL of DMSO. The poly(vinyl alcohol) is 99+% hydrolyzed, with a weight average molecular weight of 124 kDa to 186 kDa and was used as received from Sigma-Aldrich. The poly(styrene-co-allyl alcohol), with an average molecular weight of 1200 Da, was used as received from Sigma-Aldrich. The DMSO was used as received from Sigma-Aldrich and contains ≦0.4% water. The solution was heated to 90° C. for 3 hours.

After three hours, the solution was poured into a 9"×13" PYREX dish and allowed to cool to room temperature. The dish was then placed into a freezer at −30° C. for twenty-four hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

BLEND SYNTHESIS EXAMPLE 4

To a 2000-mL beaker equipped with a mechanical stirrer was added 100 g poly(ethylene-co-vinyl alcohol), 100 g poly(vinyl alcohol), and 1100 mL of DMSO. The poly(vinyl alcohol) is 99+% hydrolyzed with a weight average molecular weight of 124 kDa to 186 kDa and was used as received from Sigma-Aldrich. The poly(ethylene-co-vinyl alcohol) with an ethylene content of 27 mole-percent was used as received from Sigma-Aldrich. The DMSO was used as received from Sigma-Aldrich and contains ≦0.4% water. The solution was heated to 90° C. for three hours.

After three hours, the solution was poured into a 9"×13" PYREX dish and allowed to cool to room temperature. The dish was then placed into a freezer at −30° C. for twelve hours. The dish was removed from the freezer.

The resulting material was translucent, flexible, and pliable. To extract the DMSO, 700 mL reagent-grade alcohol (ethanol) was added to the resulting material. The material was then allowed to warm slowly to room temperature. The resulting material remained translucent, flexible, and pliable.

BLEND SYNTHESIS EXAMPLE 5

To a 2000-mL beaker equipped with a mechanical stirrer was added 100 g poly(ethylene-co-vinyl alcohol), 200 g poly(vinyl alcohol), 200 mL deionized water, and 800 mL of DMSO. The poly(vinyl alcohol) is 99+% hydrolyzed with a weight average molecular weight of 86 kDa and was used as received from Acros Organics (New Jersey). The poly(ethylene-co-vinyl alcohol) had an ethylene content of 27 mole-percent and was used as received from Sigma-Aldrich. The DMSO was used as received from Sigma-Aldrich and contains 50.4% water. The solution was heated to 90° C. for three hours.

After three hours, the solution was poured into a 9"×13" PYREX dish and a 28 mm hip cup mold. The material was allowed to cool to room temperature. The dish was then placed into a freezer at −30° C. for twelve hours. The dish was removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

BLEND SYNTHESIS EXAMPLE 6

To a 1000-mL beaker equipped with a mechanical stirrer was added 10 g poly(ethylene-co-vinyl alcohol) [44 mole-percent ethylene], 10 g poly(ethylene-co-vinyl alcohol) [27 mole-percent ethylene], 20 g poly(vinyl alcohol), 3.8 g NANODENT, and 220 mL of DMSO. The poly(vinyl alcohol) is 99+% hydrolyzed with an weight average molecular weight of 86,000 and was used as received from Acros. The poly(ethylene-co-vinyl alcohol) had an ethylene content of 27 mole-percent and 44 mole-percent, as indicated, and was used as received from Sigma-Aldrich. The DMSO was used as received from Sigma-Aldrich and contains <0.4% water. The NANODENT is a radiopacifying agent, and was used as received from NanoSolutions (Hamburg, Germany). The solution was heated to 90° C. for three hours.

After three hours, the solution was poured into a 9"×13" PYREX dish and a hip cup mold. The material was allowed to cool to room temperature. The dish was then placed into a freezer at −30° C. for twelve hours. The dish was removed from the freezer.

The material was allowed to warm to room temperature. The resulting material was translucent, flexible, and pliable. To extract the DMSO, 700 mL propanol was added to the resulting material. The resulting material remained translucent, flexible, and pliable.

BLEND SYNTHESIS EXAMPLE 7

To prepare material for a compression molder/injection molder, a HAAKE Polylab® system equipped with a Rheo-Mix was heated to 115° C. To the system was added 45 mL DMSO, 17.5 g of poly(ethylene-co-vinyl alcohol), and 17.5 g of poly(vinyl alcohol). The poly(vinyl alcohol) is 99+% hydrolyzed with a weight average molecular weight of 146 kDa to 186 kDa and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water.

The blend was allowed to mix for 10 minutes. The blend was removed from the mixer, allowed to cool to room temperature, and chopped. The resultant material was translucent and pliable.

BLEND SYNTHESIS EXAMPLE 8

A blend was prepared as in Blend Synthesis Example 7, except that the poly(ethylene-co-vinyl alcohol) had an ethylene content of 27 mole-percent.

The blend was allowed to mix for 10 minutes. The blend was removed from the mixer, allowed to cool to room temperature, and chopped. The resultant material was translucent and pliable.

BLEND SYNTHESIS EXAMPLE 9

To a 2000-mL beaker equipped with a mechanical stirrer was added 100 g poly(ethylene-co-vinyl alcohol) and 700 mL of DMSO. The poly(vinyl alcohol) is 99+% hydrolyzed with a weight average molecular weight of 146 kDa to 186 kDa and was used as received from Sigma Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water. The solution was heated to 90° C. for 12 hours.

Then, 100 g of poly(vinyl alcohol), 200 mL DMSO, and 5 g of p-toluene sulfonic acid monhydrate was added the solution as a pH modifier. The p-toluene sulfonic acid monohydrate was 98.5% pure ACS reagent-grade and was used as received from Sigma-Aldrich. The solution was heated to 90° C. for three hours.

After three hours, the solution was poured into 5" polyethylene bowls and cooled to −55° C. using a methanol/liquid nitrogen slush bath for approximately 30 minutes. A white frozen material resulted.

BLEND SYNTHESIS EXAMPLE 10

To a 2000-mL beaker equipped with a mechanical stirrer was added 150 g poly(ethylene-co-vinyl alcohol), 50 g poly(vinyl alcohol), 200 mL deionized water, and 800 mL of DMSO. The poly(vinyl alcohol) is 99+% hydrolyzed with a weight average molecular weight of 146,000 to 186,000 and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains 50.4% water. The solution was heated to 90° C. for three hours.

After three hours, the solution was poured into a 9"×13" PYREX dish and a hip cup mold. The material was allowed to cool to room temperature. The dish was then placed into a freezer at −30° C. for twelve hours. The dish was removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

BLEND SYNTHESIS EXAMPLE 11

To a 1000-mL beaker equipped with a mechanical stirrer was added 20 g poly(vinyl alcohol), 175 mL dimethyl sulfoxide, and 10 ml water. The solution was heated to 80° C. for 2 hours. To the solution was added 20 g poly(trimellitic anhydride chloride-co-4,4'-methylene-dianiline) and stirred for 1 hour at 120° C. The poly(vinyl alcohol) was 99+% hydrolyzed with an average molecular weight of 146,000 to 186,000 and was used as received from Sigma-Aldrich. The poly(trimellitic anhydride chloride-co-4,4'-methylenedianiline) was used as received from Sigma-Aldrich and contained <1.0% of 4,4'-methylenedianiline. The DMSO was used as received from Sigma-Aldrich and contains ≦0.4% water. The solution was heated to 90° C. for three hours.

The solution was poured between two 8"×8"×0.05" glass plates. The material was allowed to cool to room temperature. The dishes were then placed into a freezer at −30° C. for twelve hours. The dishes were removed from the freezer.

The material was allowed to warm to room temperature. The resulting material was translucent, flexible, and pliable. To extract the DMSO, 700 mL methanol was added to the resulting material. The resulting material remained translucent, flexible, and pliable.

BLEND SYNTHESIS EXAMPLE 12

To a Jaygo (Union, N.J.) 1 gallon sigma mixer/extruder fitted with a 3 mm fiber die was added 625.89 g poly(ethylene-co-vinyl alcohol), 100 mL water, 1350 g dimethyl sulfoxide, and 626.79 g poly(vinyl alcohol). The materials were mixed at 240° F. for 70 minutes. The poly(vinyl alcohol) is 99+% hydrolyzed with an average molecular weight of 146,000 to 186,000 and was used as received from Sigma-Aldrich. The poly(ethylene-co-vinyl alcohol) had an ethylene content of 44 mole-percent and was used as received from Sigma-Aldrich. The DMSO was used as received from Sigma-Aldrich and contains ≦0.4% water.

After 70 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

BLEND SYNTHESIS EXAMPLE 13

To a Jaygo 1 gallon sigma mixer/extruder fitted with a 3 mm fiber die was added 626.66 g poly(ethylene-co-vinyl alcohol), 128.2 mL water, 1438.2 g dimethyl sulfoxide, and 625.73 g poly(vinyl alcohol). The materials were mixed at 228° F. for 90 minutes. The poly(vinyl alcohol) is 99+% hydrolyzed with an average molecular weight of 146,000 to 186,000 and was used as received from Sigma-Aldrich. The poly(ethylene-co-vinyl alcohol) had an ethylene content of 32 mole-percent and was used as received from Sigma-Aldrich. The DMSO was used as received from Sigma-Aldrich and contains ≦0.4% water.

After 90 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

BLEND SYNTHESIS EXAMPLE 14

To a Jaygo 1 gallon sigma mixer/extruder fitted with a 3 mm fiber die was added 402.44 g poly(ethylene-co-vinyl alcohol), 97.84 mL water, 1400 g diethyl sulfoxide, and 850.02 g poly(vinyl alcohol). The materials were mixed at 228° F. for 50 minutes. The poly(vinyl alcohol) is 99+% hydrolyzed with an average molecular weight of 146,000 to 186,000 and was used as received from Sigma-Aldrich. The poly(ethylene-co-vinyl alcohol) had an ethylene content of 32 mole-percent and was used as received from Sigma-Aldrich. The DMSO was used as received from Sigma-Aldrich and contains ≦0.4% water.

After 50 minutes, the sample was extruded through a 3 mm fiber die with a draw rate of 4× and into a 50% alcohol/50% water cooling bath for a residence time of 1-3 seconds. The fiber was allowed to cool and cut into fine pellets using a fiber chopper. The resulting material remained translucent, flexible, and pliable.

Blended Hydrogel Mechanical Properties

The water-swellable materials obtained from Blend Synthesis Examples 1-6, 9, 10, and 11 were immersed in water. For the water-swellable material from Blend Synthesis Example 9, the frozen material was immersed in water while still cold, while the others were immersed at room temperature. In each case, the material took on water and became a white, opaque, flexible hydrogel.

The water-swellable materials obtained from Blend Synthesis Examples 12-14 were processed on a Battenfeld BA 100 CD injection molder with nozzle temperatures between 240° F.-280° F. and the mold at room temperature. Samples from injection molding were immersed in alcohol for a minimum of 20 minutes followed by immersion in water. In each case, the material took on water and became a white, opaque, flexible hydrogel.

The concentration of water in the resultant hydrogels were determined by thermogravimetric analysis on a TA Instruments 2950 TGA instrument. For example, the hydrogel obtained using material from Blend Synthesis Example 1 was 15% solids/85% water by weight.

Mechanical performance properties for selected hydrogels were measured, as ASTM D638 Type IV specimens, using conventional techniques on a Model 3345 instrument from Instron Corporation. Measured values are reported in Tables 1 and 2.

TABLE 1

Mechanical properties for selected solution cast hydrogels (tensile).

|  | Example 1 | Example 2 | Example 3 | Example 6 | Example 10 | Example 11 |
|---|---|---|---|---|---|---|
| Stress at Peak (psi) | 577.7 | 61.14 | 218.3 | 329.64 | 585 | 888.3 |
| Percent Strain at Peak | 342.2 | 172.20 | 686.7 | 591.5 | 517.16 | 2358.83 |
| Stress at Break (psi) | 553.4 | 57.0 | 218.31 | 316.0 | — | 871.26 |
| Percent Strain at Break | 345.5 | 175.8 | 686.7 | 591.5 | — | 2363.8 |
| Stress at 0.2% Yield (psi) | 385.85 | 15 | 199 | — | — | — |

TABLE 1-continued

Mechanical properties for selected solution cast hydrogels (tensile).

|  | Example 1 | Example 2 | Example 3 | Example 6 | Example 10 | Example 11 |
|---|---|---|---|---|---|---|
| Percent Strain at 0.2% Yield | 200.11 | 11 | 670 | — | — | — |
| Young's Modulus (ksi) | 0.305 | 0.58 | 0.161 | 0.186 | 0.251 | 62.05 |
| Energy at Yield (lbf-in) | 19.515 | 0.174 | 34.19 | 43.80 | — | 15.11 |
| Energy at Break (lbf-in) | 64.012 | 8.37 | 37.33 | 43.80 | — | 15.43 |

TABLE 2

Mechanical properties for selected injection molded hydrogels (tensile).

|  | Example 12 | Example 13 | Example 14 |
|---|---|---|---|
| Stress at Peak (psi) | 519.39 | 831.00 | 1161.98 |
| Percent Strain at Peak | 223.45 | 555.33 | 791.11 |
| Stress at Break (psi) | 497.22 | 717.06 | 1026.21 |
| Percent Strain at Break | 233.67 | 571.33 | 808.89 |
| Stress at 0.2% Yield (psi) | — | — | — |
| Percent Strain at 0.2% Yield | — | — | — |
| Young's Modulus (ksi) | 711.20 | 344.92 | 354.57 |
| Energy at Yield (lbf-in) | 2.305 | 9.19 | 13.68 |
| Energy at Break (lbf-in) | 2.456 | 9.59 | 20.15 |

Irradiation can be used as a means of crosslinking the samples. Two sets of injection molded tensile specimens from Blend 14 were gamma irradiated at a dose between 26.3-34.0 kGy. The strengths of the irradiated samples are shown in Table 3.

TABLE 3

Mechanical properties for selected irradiated hydrogels (tensile).

|  | Example 14 | Example 14 |
|---|---|---|
| Injection Molding Temperature, nozzle (° F.) | 255 | 260 |
| Tensile Strength (psi) | 961.70 | 1121.50 |
| Initial Elastic Modulus | 353.96 | 316.48 |
| Strain at Break (%) | 566.88 | 1337.50 |
| Toughness (%) | 3508.81 | 9837.50 |
| Water Content (%) | 45.5 | 45.0 |

Characterization

Hydrogels prepared using material from Blend Synthesis Examples 1 and 10 were tested on a MATCO load frame equipped with a standard shoulder head. The hydrogels were tested for shear under a loading of 175 lbs.

The hydrogel from Blend Synthesis 1 was tested for a simulated 1 year period and 2 mm displacement, and showed no sign of shearing. Some creep was observed.

The hydrogel from Blend 10 was tested for a simulated 7.5 year period and a 1 mm displacement, and also showed no signs of shearing. Some creep was observed.

Rheological tests were performed on a TA Instruments AR-1000 rheometer using a parallel plate geometry and swollen hydrogel disks with a diameter of 25 mm and a thickness of 1.5 mm. All tests were performed at room temperature unless otherwise indicated. A normal force of 1-2 N was applied. First, a strain sweep test was conducted to find the linear region (0.01-0.03%) and then a frequency scan (1-50 Hz) was performed with a strain of 0.01%. As shown in Table 4, Blend Synthesis 1 has a higher shear modulus (G*) than that of the nucleus pulposus but lower than that of the articular cartilage.

TABLE 4

Comparison of the shear viscoelastic properties between Blend Synthesis 1 and Human nucleus pulposus

| Material | Frequency (rad/s/Hz) | G*(kPa) | Tan delta (degree) |
|---|---|---|---|
| Blend Synthesis 1 | 10/1.58 | 149-340 | 5.6 |
| Nucleus pulposus | 10/1.58 | 11 | 24 |
| Articular cartilage | 10/1.58 | 600-1000 | 13 |

Crystallinity and phase separation were analyzed on a TA Instruments DSC Q1000 instrument utilizing pressure pans and a heating rate of 10° C./min. Analysis shows that the blends were homogeneous with only one glass transition peak and no crystallinity peaks. After hydration, the blends show crystallinity peaks. For example, blend synthesis 1 has a Tg of 48° C. in the dry state and no apparent crystallinity peaks. In the hydrated state, Blend Synthesis 1 has a melt peak at 98° C. with an exotherm area representing 2.03% crystallinity. The melting point of 98° C. corresponds to the melting point of the polyethylene.

Use of Thermoplastic Material

The water-swellable material obtained following the procedure set forth in Blend Synthesis Example 1 was shaped and placed into an ADHESIVE TECH® Model 229 Low Temp Glue Gun. The working temperature of the glue gun was 127° C. The material was extruded from the gun to a variety of substrates and environments, including onto paper, into open air, and into water (room temperature).

It was observed that the material, although extruded at a temperature over 100° C., could be handled manually without special precautions. The material cooled quickly to near room temperature.

While still hot immediately following extrusion, the material is translucent and colorless, and the shape can be modified using, for example, a spatula as a means to spread the material. The extruded material can be subsequently hydrated by contact with or immersion in water or an aqueous solution. When the material is hydrated, it gradually turns from translucent to opaque white. The development of the white color is thought to indicate the formation of crystalline regions.

Kuralon® REC series available from Kuraray Co. Ltd. (Japan). The PVA fibers were irradiated prior to use. The DMSO, obtained from Sigma Aldrich, contained ≦0.4% water.

After mixing for 5 minutes, the sample was removed, cooled to room temperature, and chopped into flake form for use in the Battenfeld BA 100 CD injection molder machine. The resulting material remained translucent, flexible, and pliable.

TABLE 5

Fiber-Reinforced Hydrogel Examples 1-23

| Fiber-Reinforced Hydrogel Example | PVA | Poly(ethylene-co-vinyl alcohol) | Water | DMSO | Fiber | Fiber (Diameter × Length) | Dose | % PVA | % Fiber | Post Crosslinked |
|---|---|---|---|---|---|---|---|---|---|---|
| 1 | 33.25 | — | 7 | 28 | 1.75 | 15 × 18 | 25 | 47.50 | 2.50 | — |
| 2 | 33.25 | — | 7 | 28 | 1.75 | 100 × 12 | 25 | 47.50 | 2.50 | — |
| 3 | 34.65 | — | 7 | 28 | 0.35 | 15 × 18 | 50 | 49.50 | 0.50 | — |
| 4 | 33.25 | — | 7 | 28 | 1.75 | 100 × 12 | 50 | 47.50 | 2.50 | — |
| 5 | 20 | — | 9.8 | 39.2 | 1 | 100 × 12 | 25 | 28.57 | 1.43 | — |
| 6 | 33.25 | — | 7 | 28 | 1.75 | 7 × 6 | 50 | 47.50 | 2.50 | — |
| 7 | 31.5 | — | 7 | 28 | 3.5 | 15 × 18 | 50 | 45.00 | 5.00 | — |
| 8 | 33.25 | — | 7 | 28 | 1.75 | 15 × 18 | 50 | 47.50 | 2.50 | — |
| 9 | 16 | — | 8.4 | 33.6 | 12 | 15 × 18 | 25 | 22.86 | 17.14 | — |
| Comparative 10 | 35 | — | 7 | 28 | 0 | — | — | 50.00 | — | — |
| 11 | 35 | — | 7 | 28 | 0 | — | — | 50.00 | — | — |
| 12 | 31.5 | — | 6.3 | 25.2 | 10 | 100 × 12 | 50 | 43.15 | 13.70 | — |
| 13 | 14 | 17.5 | 7 | 28 | 3.5 | 7 × 6 | 50 | 20.00 | 5.00 | — |
| Comparative 14 | 14 | 17.5 | 7 | 28 | 0 | — | 50 | 21.05 | — | — |
| 15 | 33.25 | — | 7 | 28 | 1.75 | 100 × 12 | 25 | 47.5 | 2.5 | Freeze Thaw |
| 16 | 34.65 | — | 7 | 28 | 0.35 | 15 × 18 | 50 | 49.5 | 0.5 | Freeze Thaw |
| 17 | 33.25 | — | 7 | 28 | 1.75 | 15 × 18 | 25 | 47.5 | 2.5 | Irradiation |
| 18 | 33.25 | — | 7 | 28 | 1.75 | 100 × 12 | 25 | 47.5 | 2.5 | Irradiation |
| 19 | 34.65 | — | 7 | 28 | 0.35 | 15 × 18 | 50 | 49.5 | 0.5 | Irradiation |
| 20 | 33.25 | — | 7 | 28 | 1.75 | 100 × 12 | 50 | 47.5 | 2.5 | Irradiation |
| 21 | 33.25 | — | 7 | 28 | 1.75 | 7 × 6 | 50 | 47.5 | 2.5 | Irradiation |
| 22 | 31.5 | — | 7 | 28 | 3.5 | 15 × 18 | 50 | 45 | 5.0 | Irradiation |
| 23 | 33.25 | — | 7 | 28 | 1.75 | 15 × 18 | 50 | 47.5 | 2.5 | Irradiation |

Splittable Microfibers

The water-swellable material obtained from blends 12-14 spontaneously formed splittable microfibers during the extrusion process. The strands were 2-4 mm in diameter and composed of individual fibers with a diameter of 2-9 nm as determined by scanning electron microscopy. The individual fiber strands could be separated using mechanical or thermal treatments. Furthermore, the strands could be processed utilizing alcohol treatment followed by water exchange to create the hydrogel microfibers.

Examples of Fiber-Reinforced Hydrogels

The general procedures and processes for making fiber-reinforced hydrogels (Examples 1-23) are described below. Table 5 shows the amount of each material used in the Examples. The amount of PVA and PVA fibers are provided in grams, the water and DMSO in milliters and the fiber diameter in denier and length in millimeters. The fibers were irradiated using gamma irradiation at Sterigenics (Charlotte, N.C.) at either 25+/−3 kGy or 50+/−3 kGy dose.

To a Haake Polylab® twin screw rheometer was added PVA, water, DMSO, and PVA fiber. The materials were mixed at 120° C. for 5 minutes. The PVA, obtained from Sigma Aldrich, is 99+% hydrolyzed with an average molecular weight of 146,000 to 186,000 kDa. The poly(ethylene-covinyl alcohol) was used as received from Sigma Aldrich and contained 44% ethylene. The PVA fibers used are the

EXAMPLES 1-14

Figure 3:
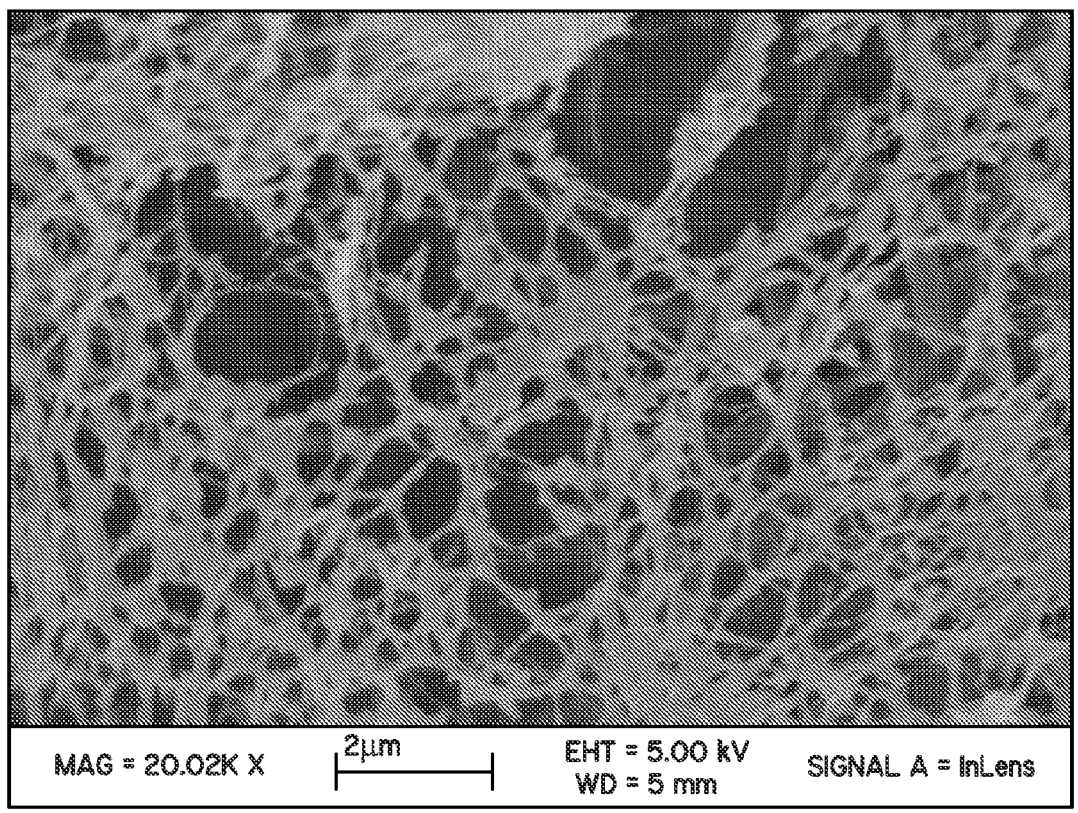
FIG. 3 shows a scanning electron micrograph of a hydrogel in one embodiment of the invention.
Figure 4:
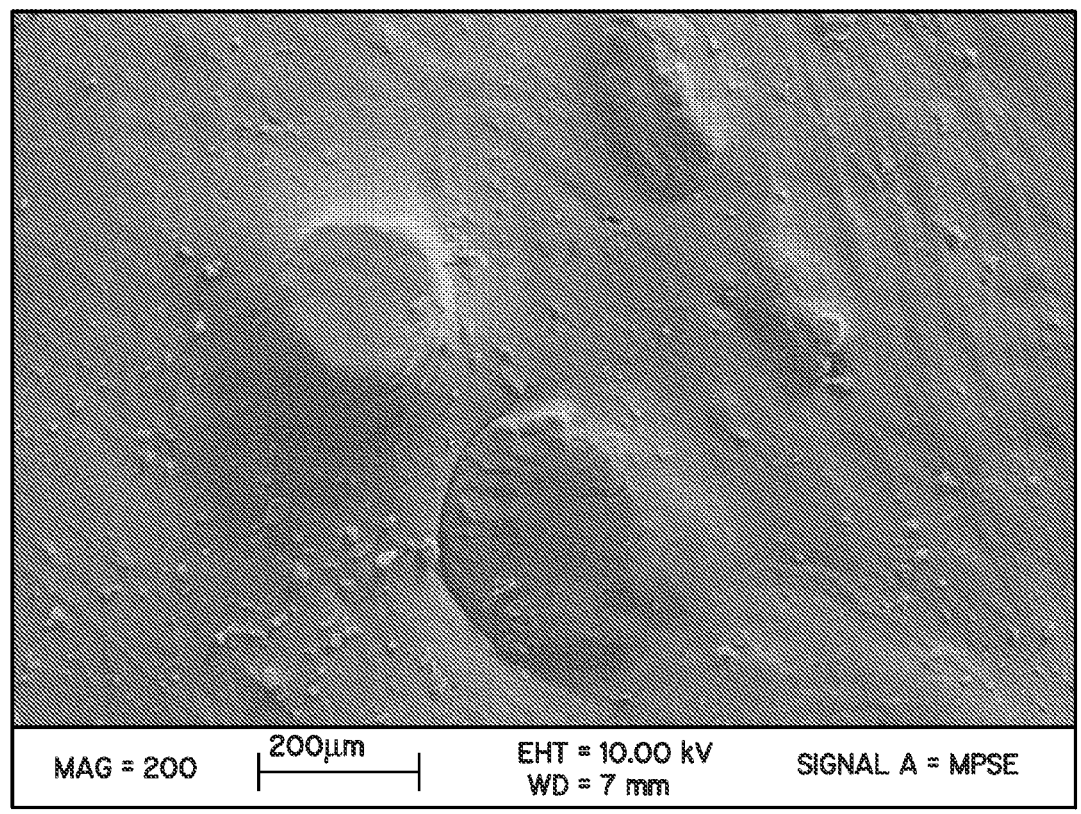
FIG. 4 shows a scanning electron micrograph of a hydrogel in another embodiment of the invention.

The translucent, flexible, and pliable material obtained from Examples 1-10 were further processed on a Battenfeld BA 100 CD injection molder with nozzle temperatures between 240° F.-280° F. and the mold at room temperature. Samples from injection molding were first immersed in alcohol for a minimum of 20 minutes followed by immersion in water. Samples 1-10 were immersed in 80° C. water for 20 minutes followed by room temperature water for 2 days. Samples 11-14 were immersed only in room temperature water for 2 days. Fibers could be seen by the naked eye. Some fiber alignment was present in the direction of melt flow. FIGS. 3 and 4 show the incorporation of fibers into the gel matrix in two embodiments of the invention. FIG. 3 shows a scanning electron microscopy (SEM) photo of Example 2 indicating that the residual fibers are intact after processing. Similarly, FIG. 4 shows a SEM photo of Example 9, also indicating that the residual fibers are intact after processing.

EXAMPLE 15

The water-swellable material obtained from Example 2 was processed on a Battenfeld BA 100 CD injection molder to form a tensile bar and compression molded sample specimens. The specimens were immersed in alcohol for a minimum of 20 minutes followed by immersion in 80° C. water for 20 minutes. The samples were then allowed to solvent exchange in deionized water at room temperature for 2 days. The samples were exposed three times to a repetitive freeze-thaw cycle. In the cycle, the samples were frozen by placing in a freezer at −30° C. for 12 hours followed by thawing at room temperature for 12 hours.

EXAMPLE 16

The water-swellable material obtained from Example 3 was processed as described in Example 15.

EXAMPLE 17

The water-swellable material obtained from Example 1 was nitrogen-packed and irradiated at 75 kGy at Sterigenics in Charlotte, N.C. Samples were then allowed to rehydrate for one day in deionized water prior to testing.

EXAMPLE 18

The water-swellable material obtained from Example 2 was processed as described in Example 17.

EXAMPLE 19

The water-swellable material obtained from Example 3 was processed as described in Example 17.

EXAMPLE 20

The water-swellable material obtained from Example 4 was processed as described in Example 17.

EXAMPLE 21

The water-swellable material obtained from Example 6 was processed as described in Example 17.

EXAMPLE 22

The water-swellable material obtained from Example 7 was processed as described in Example 17.

EXAMPLE 23

The water-swellable material obtained from Example 8 was processed as described in Example 17.

Mechanical performance properties for selected hydrogels were measured using the American Society of Testing Materials standards (ASTM D638 Type IV specimens) and using conventional techniques on a Model 3345 from Instron Corporation. Tensile specimens were kept hydrated during the test using a peristaltic pump with a rate of 60 drops per second. Compression testing was performed on a Model 3345 from Instron Corporation in a water bath at room temperature. Compression samples were in cylinders of 0.25×0.25 inches. Measured values for tensile properties are reported in Table 6. Measured values for compressive properties are reported in Table 7.

TABLE 6

Tensile Properties For Selected Crosslinked Fiber Hydrogels.

|  | Stress at Peak (psi) | Percent Strain at Peak | Stress at Break (psi) | Percent Strain at Break | Young's Modulus (ksi) | Energy at Yield (lbf-in) | Energy at Break (lbf-in) |
|---|---|---|---|---|---|---|---|
| Example 1 | 366 | 199 | 259 | 224 | 0.29 | 0.52 | 2.70 |
| Example 2 | 500 | 168 | 296 | 190 | 0.43 | 0.97 | 2.92 |
| Example 3 | 418 | 169 | 301 | 186 | 0.34 | 0.39 | 2.41 |
| Example 4 | 434 | 133 | 281 | 157 | 0.42 | 0.64 | 2.23 |
| Example 5 | 186 | 340 | 131 | 370 | 0.11 | 0.90 | 2.14 |
| Example 6 | 462 | 145 | 274 | 166 | 0.39 | 0.74 | 2.54 |
| Example 7 | 356 | 136 | 276 | 154 | 0.60 | 0.96 | 1.91 |
| Example 8 | 466 | 158 | 283 | 183 | 0.37 | 0.75 | 2.79 |
| Example 9 | 315 | 312 | 167 | 347 | 0.16 | 1.69 | 2.86 |
| Example 10 (Control for 1-4, 6-8) | 191 | 277 | 107 | 317 | 0.17 | 1.63 | 2.27 |
| Example 11 | 450 | 278 | 338 | 278 | 0.29 | 1.39 | 3.63 |
| Example 12 | 694 | 176 | 437 | 208 | 0.55 | 1.07 | 3.37 |
| Example 13 | 1074 | 305 | 871 | 322 | 664.40 | 2.46 | 7.76 |
| Example 14 (Control for 12) | 831 | 555 | 717 | 57 | 344.92 | 9.19 | 9.59 |

TABLE 7

Selected Compressive Properties Of Crosslinked Fiber Hydrogels.

| | Compressive Tangent Modulus at Different Strain Levels (psi) | | | | |
|---|---|---|---|---|---|
|  | 20% Strain | 30% Strain | 40% Strain | 60% Strain | 70% Strain |
| Example 1 | 823.9 | 976.4 | 1286.9 | 3018.3 | 8035.6 |
| Example 2 | 751.8 | 912.4 | 1225.7 | 3303.3 | 8416.9 |
| Example 3 | 649.4 | 832.9 | 1150.7 | 2649.6 | 6630.4 |
| Example 4 | 868.4 | 1030.4 | 1382.1 | 3535.0 | 8841.5 |
| Example 5 | 531.2 | 656.6 | 872.2 | 1958.2 | 5167.2 |

TABLE 7-continued

Selected Compressive Properties Of Crosslinked Fiber Hydrogels.

| | Compressive Tangent Modulus at Different Strain Levels (psi) | | | | |
|---|---|---|---|---|---|
| | 20% Strain | 30% Strain | 40% Strain | 60% Strain | 70% Strain |
| Example 6 | 1060.2 | 1227.3 | 1653.0 | 4584.6 | 10431.2 |
| Example 7 | 804.3 | 913.9 | 1242.6 | 3045.2 | 7426.5 |
| Example 8 | 898.4 | 1026.2 | 1349.8 | 3459.2 | 8260.7 |
| Example 9 | 549.6 | 690.9 | 787.9 | 1839.8 | 4581.6 |
| Example 10 (Control for 1-4, 6-8) | 331.5 | 478.0 | 730.3 | 2036.9 | 5029.4 |
| Example 11 | 2302.1 | 2180.3 | 2230.3 | 3136.4 | — |
| Example 12 (Control for 11) | 1670.2 | 1770.0 | 1860.8 | 2806.5 | 4737.0 |
| Example 13 | 2302.1 | 2180.3 | 2230.3 | 3136.4 | — |
| Example 14 (Control for 13) | 1670.2 | 1770.0 | 1860.8 | 2806.5 | 4737.0 |
| Example 15 | 651.6 | 862.6 | 1242.4 | 3082.6 | 7200.0 |
| Example 16 | 527.4 | 747.3 | 1094.4 | 2516.9 | 1215.4 |

TABLE 8

Tensile Properties For Selected Crosslinked Fiber Hydrogels After 75 Kgy Post Irradiation.

| | Stress at Peak (psi) | Percent Strain at Peak | Stress at Break (psi) | Percent Strain at Break | Young's Modulus (ksi) | Energy at Yield (lbf-in) | Energy at Break (lbf-in) |
|---|---|---|---|---|---|---|---|
| Example 17 | 277 | 120 | 113 | 156 | 0.32 | 0.21 | 1.13 |
| Example 18 | 417 | 115 | 279 | 139 | 0.48 | 0.42 | 1.50 |
| Example 19 | 456 | 148 | 324 | 163 | 0.58 | 0.64 | 2.29 |
| Example 20 | 494 | 123 | 324 | 143 | 0.52 | 0.53 | 2.05 |
| Example 21 | 526 | 146 | 322 | 163 | 0.46 | 0.73 | 2.33 |
| Example 22 | 210 | 85 | 92 | 122 | 0.35 | 0.09 | 0.81 |
| Example 23 | 315 | 83 | 208 | 107 | 0.53 | 0.30 | 1.11 |

The results set forth in Tables 6, 7, and 8 indicate that samples containing crosslinked fibers possessed certain improved mechanical characteristics over the control samples. The data showed that the material had become stiffer, showed less elongation and was more crosslinked after post irradiation.

The invention is further set forth in the claims listed below. This invention may take on various modifications and alterations without departing from the spirit and scope thereof. In describing embodiments of the invention, specific terminology is used for the sake of clarity. The invention, however, is not intended to be limited to the specific terms so selected, and it is to be understood that each term so selected includes all technical equivalents that operate similarly.

What is claimed is:

1. A method of bonding a hydrogel component to a surface, comprising: contacting the surface and the hydrogel component; and selectively irradiating a region at an interface of the hydrogel component and the surface using a laser emitting light at a wavelength in the range of 900 nm-1,600 nm, inclusive, to bond the hydrogel component to the surface.

2. The method of claim 1 wherein the hydrogel component comprises at least one polymer containing hydroxyl or one or more carboxylic acid groups.

3. The method of claim 1 wherein the hydrogel component comprises at least one polymer that is poly(vinyl alcohol) or a derivative thereof.

4. The method of claim 1 wherein the hydrogel component comprises a blend of polymers.

5. A method of bonding, comprising shaping a hydrogel component to provide a hydrogel article configured for joint repair; contacting a surface and the hydrogel article; and selectively irradiating a region at an interface of the hydrogel article and the surface to bond the hydrogel article to the surface.

6. The method of claim 5 wherein the hydrogel article is shaped to include at least one cylindrical, spherical, or polyhedral segment.

7. The method of claim 5 wherein the surface is a soft tissue surface.

8. The method of claim 7 wherein the soft tissue surface is at a collagen site, joint site, an articulating surface site or a load-bearing surface site.

9. The method of claim 5 wherein the surface is a hydrogel article surface.

10. The method of claim 5 wherein the hydrogel component is either a preformed hydrogel or a hydrogel precursor.

11. The method of claim 5 wherein the hydrogel component is a blend of polymers.

12. The method of claim 5 wherein the hydrogel component is fiber reinforced.

13. The method of claim 1 wherein the hydrogel component is flowable.

14. A method of making a cross-linked gradient in a hydrogel article using a layering process, the method comprising:
selectively irradiating one or more predetermined reoions of a first hydrogel component in a first predetermined pattern to provide a first patterned layer;

contacting the first patterned layer with a second layer of hydrogel component; and selectively irradiating one or more predetermined regions of the second layer of the hydrogel component in a second predetermined pattern that is the same or different than the first predetermined pattern;

wherein the irradiated regions have a greater concentration of cross-linking than in one or more non-irradiated regions.

15. The method of claim 14 wherein the one or more pre-determined regions include at least one rasterized pattern.

16. The method of claim 14 wherein the one or more pre-determined regions include at least one geometric pattern.

17. The method of claim 14 wherein a laser is used to selectively irradiate the hydrogel article.

18. The method of claim 14 wherein the cross-linked gradient comprises at least one three-dimensional pattern.

19. The method of claim 14 wherein the layering process is repeated a predetermined number of times.

20. The method of claim 14 wherein at least one surface of the first hydrogel layer is bonded to a contacting surface of the second hydrogel layer.

* * * * *

UNITED STATES PATENT AND TRADEMARK OFFICE
CERTIFICATE OF CORRECTION

| | | |
|---|---|---|
| PATENT NO. | : 8,262,730 B2 | |
| APPLICATION NO. | : 11/608128 | |
| DATED | : September 11, 2012 | |
| INVENTOR(S) | : Thomas et al. | |

It is certified that error appears in the above-identified patent and that said Letters Patent is hereby corrected as shown below:

On the Title Page: Item (56) References Cited, in column 2, under "Other Publications", line 1, before "Ocacalcium", insert --"--, therefor On the Title Page: In column 2, under "Other Publications", line 1, after "Phosphate", insert --"--, therefor On page 2, in column 2, under "U.S. Patent Documents", line 6, in the citation for U.S. PATENT "6,232,406 5/2001 Ku" After "Stoy", delete "et al.", therefor On page 3, in column 2, under "Other Publications", line 5, delete "R.Z.," and insert --R. Z.,--, therefor On page 3, in column 2, under "Other Publications", line 21, before "Poly(vinyl Alcohol)", insert --"--, therefor On page 3, in column 2, under "Other Publications", line 22, after "Biocompatibility", insert --"--, therefor On page 3, in column 2, under "Other Publications", line 23, after "vol. 2", insert --,--, therefor On page 3, in column 2, under "Other Publications", line 24, delete "Hassan," and insert --Hassan--, therefor On page 3, in column 2, under "Other Publications", line 24, before "Structure", insert --"--, therefor On page 3, in column 2, under "Other Publications", line 26, after "Methods,", insert --"--, therefor On page 3, in column 2, under "Other Publications", line 28, delete "Peppas," and insert --Peppas--, therefor Signed and Sealed this
Eleventh Day of December, 2012

David J. Kappos
*Director of the United States Patent and Trademark Office*

On page 3, in column 2, under "Other Publications", line 28, before "Physicochemical", insert --"--, therefor On page 3, in column 2, under "Other Publications", line 29, after "Biology,", insert --"--, therefor On page 3, in column 2, under "Other Publications", line 31, delete "Taguchi." and insert --Taguchi,--, therefor On page 3, in column 2, under "Other Publications", line 32, delete "al." and insert --al.,--, therefor On page 3, in column 2, under "Other Publications", line 33, delete "al." and insert --al.,--, therefor On page 3, in column 2, under "Other Publications", line 34, delete "al." and insert --al.,--, therefor On page 3, in column 2, under "Other Publications", line 36, delete "al." and insert --al.,--, therefor On page 3, in column 2, under "Other Publications", line 39, delete "al." and insert --al.,--, therefor On page 3, in column 2, under "Other Publications", line 41, delete "al." and insert --al.,--, therefor On page 4, in column 1, under "Other Publications", line 1, delete "S.J. et al." and insert --S. J. et al.,--, therefor On page 4, in column 1, under "Other Publications", line 5, delete "S.J. et al." and insert --S. J. et al.,--, therefor On page 4, in column 1, under "Other Publications", line 8, delete "S.J. et al." and insert --S. J. et al.,--, therefor On page 4, in column 1, under "Other Publications", line 13, delete "al." and insert --al.,--, therefor On page 4, in column 1, under "Other Publications", line 15, delete "J.P. et al." and insert --J. P. et al.,--, therefor On page 4, in column 1, under "Other Publications", line 18, delete "al." and insert --al.,--, therefor On page 4, in column 1, under "Other Publications", line 22, delete "C.M. et al." and insert --C. M. et al.,--, therefor On page 4, in column 1, under "Other Publications", line 25, delete "C.M. et al." and insert --C. M. et al.,--, therefor On page 4, in column 1, under "Other Publications", line 28, delete "A.S. et al." and insert --A. S. et al.,--, therefor On page 4, in column 1, under "Other Publications", line 31, delete "al." and insert --al.,--, therefor On page 4, in column 1, under "Other Publications", line 35, delete "al." and insert --al.,--, therefor On page 4, in column 1, under "Other Publications", line 38, delete "C.L. et al." and insert --C. L. et al.,--, therefor On page 4, in column 1, under "Other Publications", line 41, delete "al." and insert --al.,--, therefor On page 4, in column 1, under "Other Publications", line 44, delete "J.H. et al." and insert --J. H. et al.,--, therefor On page 4, in column 1, under "Other Publications", line 48, delete "R.H. et al." and insert --R. H. et al.,--, therefor On page 4, in column 1, under "Other Publications", line 51, delete "L.J. et al." and insert -- L. J. et al.,--, therefor On page 4, in column 1, under "Other Publications", line 54, delete "J.D." and insert --J. D.,--, therefor On page 4, in column 1, under "Other Publications", line 57, delete "al." and insert --al.,--, therefor On page 4, in column 1, under "Other Publications", line 60, delete "al." and insert --al.,--, therefor On page 4, in column 1, under "Other Publications", line 63, delete "al." and insert --al.,--, therefor On page 4, in column 1, under "Other Publications", line 71, delete "8pp." and insert --8 pp.--, therefor On page 4, in column 1, under "Other Publications", line 72, delete "C.M." and insert --C. M.--, therefor On page 4, in column 1, under "Other Publications", line 72, before "Diffusional", insert --"--, therefor On page 4, in column 2, under "Other Publications", line 1, after "devices", insert --"--, therefor On page 4, in column 2, under "Other Publications", line 3, before "Synthesis", insert --"--, therefor On page 4, in column 2, under "Other Publications", line 5, after "Chemistry", insert --"--, therefor On page 4, in column 2, under "Other Publications", line 7, before "Laser", insert --"--, therefor On page 4, in column 2, under "Other Publications", line 9, after "Medicine", insert --"--, therefor On page 4, in column 2, under "Other Publications", line 14, delete "2008;" and insert --2008,--, therefor

CERTIFICATE OF CORRECTION (continued)
U.S. Pat. No. 8,262,730 B2

On page 4, in column 2, under "Other Publications", line 15, delete "J.C. et al." and insert --J. C. et al.,--, therefor On page 4, in column 2, under "Other Publications", line 15, delete "Alcohool" and insert --Alcohol--, therefor On page 4, in column 2, under "Other Publications", line 19, delete "J.C. et al." and insert --J. C. et al.,--, therefor On page 4, in column 2, under "Other Publications", line 22, delete "K." and insert --K.,--, therefor On page 4, in column 2, under "Other Publications", line 22, before "Thermodynamic", insert --"--, therefor On page 4, in column 2, under "Other Publications", line 23, after "Solutions.", insert --"--, therefor On page 4, in column 2, under "Other Publications", line 25, delete "V.I. et al." and insert --V. I. et al.,--, therefor On page 4, in column 2, under "Other Publications", line 29, delete "V.I. et al." and insert --V. I. et al.,--, therefor On page 4, in column 2, under "Other Publications", line 32, delete "V.I. et al." and insert --V. I. et al.,--, therefor On page 4, in column 2, under "Other Publications", line 35, delete "al." and insert --al.,--, therefor On page 4, in column 2, under "Other Publications", line 35, delete "Uncrosslinkable" and insert --Uncrosslinked--, therefor On page 4, in column 2, under "Other Publications", line 38, delete "A.V. et al." and insert --A. V. et al.,--, therefor On page 4, in column 2, under "Other Publications", line 41, delete "F." and insert --F.,--, therefor On page 4, in column 2, under "Other Publications", line 41, before "Swelling", insert --"--, therefor On page 4, in column 2, under "Other Publications", line 42, after "Hydrogels.", insert --"--, therefor On page 4, in column 2, under "Other Publications", line 43, delete "V.I" and insert --V. I.,--, therefor On page 4, in column 2, under "Other Publications", line 46, delete "F." and insert --F.,--, therefor
On page 4, in column 2, under "Other Publications", line 49, delete "R.J. et al." and insert --R. J. et al.,--, therefor On page 4, in column 2, under "Other Publications", line 52, delete "Yee." and insert --Yee,-- therefor On page 4, in column 2, under "Other Publications", line 52, before "Characterisation", insert --"--, therefor On page 4, in column 2, under "Other Publications", line 52, after "Hydrogel,", insert --"--, therefor On page 4, in column 2, under "Other Publications", line 56, delete "1009" and insert --2009--, therefor On page 4, in column 2, under "Other Publications", line 57, delete "J." and insert --J.,-- therefor On page 4, in column 2, under "Other Publications", line 59, delete "etal." and insert --et al.,--, therefor On page 4, in column 2, under "Other Publications", line 64, delete "et al." and insert --et al.,--, therefor On page 4, in column 2, under "Other Publications", line 65, delete "et al." and insert --et al.,--, therefor On page 4, in column 2, under "Other Publications", line 66, delete "et al." and insert --et al.,--, therefor On page 4, in column 2, under "Other Publications", line 69, delete "et al." and insert --et al.,--, therefor On page 5, in column 1, under "Other Publications", line 1, delete "et al." and insert --et al.,--, therefor On page 5, in column 1, under "Other Publications", line 2, delete "b" and insert --by--, therefor On page 5, in column 1, under "Other Publications", line 9, delete "al." and insert --al.,--, therefor On page 5, in column 1, under "Other Publications", line 11, delete "al." and insert --al.,--, therefor On page 5, in column 1, under "Other Publications", line 14, delete "al." and insert --al.,--, therefor On page 5, in column 1, under "Other Publications", line 14, delete ":Solute" and insert --"Solute--, therefor On page 5, in column 1, under "Other Publications", line 16, after "techniques.", insert --"--, therefor On page 5, in column 1, under "Other Publications", line 17, delete "et al." and insert --et al.,--, therefor

CERTIFICATE OF CORRECTION (continued)
U.S. Pat. No. 8,262,730 B2

On page 5, in column 1, under "Other Publications", line 17, before "The", insert --"--, therefor On page 5, in column 1, under "Other Publications", line 19, after "Solution.", insert --"--, therefor On page 5, in column 1, under "Other Publications", line 20, delete "2000." and insert --2000,--, therefor On page 5, in column 1, under "Other Publications", line 22, after "1999", insert --,--, therefor On page 5, in column 2, under "Other Publications", line 1, delete "et al." and insert --et al.,--, therefor On page 5, in column 2, under "Other Publications", line 1, before "Mechanical", insert --"--, therefor On page 5, in column 2, under "Other Publications", line 2, after "Biomaterials.", insert --"--, therefor On page 5, in column 2, under "Other Publications", line 2, after "2001", insert --,--, therefor On page 5, in column 2, under "Other Publications", line 4, delete "et al." and insert --et al.,--, therefor On page 5, in column 2, under "Other Publications", line 4, before "Properties", insert --"--, therefor On page 5, in column 2, under "Other Publications", line 5, after "solution.", insert --"--, therefor On page 5, in column 2, under "Other Publications", line 6, delete "Science 1989 37" and insert --Science, 1989, 37--, therefor On page 5, in column 2, under "Other Publications", line 7, delete "I." and insert --I.,--, therefor On page 5, in column 2, under "Other Publications", line 7, delete "G." and insert --G.,--, therefor On page 5, in column 2, under "Other Publications", line 7, before "Study", insert --"--, therefor On page 5, in column 2, under "Other Publications", line 9, after "formation.", insert --"--, therefor On page 5, in column 2, under "Other Publications", line 11, delete "M et al." and insert --M. et al.,--, therefor On page 5, in column 2, under "Other Publications", line 12, after "2000", insert --,--, therefor On page 5, in column 2, under "Other Publications", line 14, delete "et al." and insert --et al.,--, therefor On page 5, in column 2, under "Other Publications", line 17, before "Glossary", insert --"--, therefor

CERTIFICATE OF CORRECTION (continued)
U.S. Pat. No. 8,262,730 B2

On page 5, in column 2, under "Other Publications", line 17, after "IUPAC,", insert --"--, therefor In the Claims:

In column 25, line 55, in claim 1, after "comprising:", insert --¶--, therefor

In column 25, line 56, in claim 1, after "and", insert --¶--, therefor

In column 26, line 38, in claim 5, delete "comprising" and insert --comprising:¶--, therefor In column 26, line 40, in claim 5, after "repair;", insert --¶--, therefor In column 26, line 40, in claim 5, after "and", insert --¶--, therefor In column 26, line 51, in claim 8, after "site,", insert --a--, therefor In column 26, line 65, in claim 14, delete "reoions" and insert --regions--, therefor